(12) United States Patent
Gravenstein et al.

(10) Patent No.: US 9,881,133 B2
(45) Date of Patent: Jan. 30, 2018

(54) PATIENT IN-THE-LOOP PARTICIPATORY CARE AND MONITORING

(71) Applicant: UNIVERSITY OF FLORIDA RESEARCH FOUNDATION, INCORPORATED, Gainesville, FL (US)

(72) Inventors: Nikolaus Gravenstein, Gainesville, FL (US); Samsun Lampotang, Gainesville, FL (US); David Lizdas, Gainesville, FL (US); Yashwant Singh Bisht, Seattle, WA (US); Wilhelm K. Schwab, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 24 days.

(21) Appl. No.: 14/400,525

(22) PCT Filed: May 17, 2013

(86) PCT No.: PCT/US2013/041590
§ 371 (c)(1),
(2) Date: Nov. 11, 2014

(87) PCT Pub. No.: WO2013/173712
PCT Pub. Date: Nov. 21, 2013

(65) Prior Publication Data
US 2015/0137988 A1 May 21, 2015

Related U.S. Application Data

(60) Provisional application No. 61/649,165, filed on May 18, 2012.

(51) Int. Cl.
*G08C 15/06* (2006.01)
*G06F 19/00* (2011.01)
(Continued)

(52) U.S. Cl.
CPC ......... *G06F 19/3418* (2013.01); *A61B 5/002* (2013.01); *A61B 5/14551* (2013.01);
(Continued)

(58) Field of Classification Search
None
See application file for complete search history.

(56) References Cited

U.S. PATENT DOCUMENTS 6,047,203 A * 4/2000 Sackner ............. A41D 13/1281
600/301
6,807,965 B1 10/2004 Hickle
(Continued)

OTHER PUBLICATIONS

"International Search Report & Written Opinion for PCT Patent Application No. PCT/US2013/041590", dated Aug. 27, 2013, dated May 17, 2013, 15 Pages.

*Primary Examiner* — Adolf Dsouza
(74) *Attorney, Agent, or Firm* — Saliwanchik, Lloyd & Eisenschenk

(57) ABSTRACT

Methods and systems for patient participatory care and monitoring are provided for applications including respiratory care, ECG monitoring, capnography, infusion pump alarm prevention/management, pressure sore prevention, incentive spirometry, consciousness monitoring during sedation, pain management and other care and monitoring modalities. A patient in-the-loop system includes an input interface for receiving data acquired from a monitoring, controlling or sensing device, a storage device for storing the data at a first location, and a processor for analyzing artifacts in the data and determining whether the patient provided a deliberate action with respect to the device as a response to a prompt or query. The processor can further initiate a variety of prompts and/or output queries stored in the storage device at a second location to the patient. The data derived from these patient-in-the-loop techniques are for- (Continued)

matted to be received and interpreted by electronic medical record and electronic record keeping systems.

29 Claims, 15 Drawing Sheets

(51) Int. Cl.
    *A61B 5/00*     (2006.01)
    *A61B 5/1455*     (2006.01)
    *G01F 15/06*     (2006.01)
    *G01N 33/49*     (2006.01)

(52) U.S. Cl.
    CPC .......... *A61B 5/7207* (2013.01); *A61B 5/7267* (2013.01); *A61B 5/7296* (2013.01); *A61B 5/7405* (2013.01); *G01F 15/063* (2013.01); *G01N 33/4925* (2013.01); *A61B 5/447* (2013.01); *F04C 2270/041* (2013.01)

(56) References Cited

U.S. PATENT DOCUMENTS

| | | | |
|---|---|---|---|
| 2003/0145854 A1* | 8/2003 | Hickle | A61M 16/0084 128/204.18 |
| 2004/0129271 A1 | 7/2004 | Hickle | |
| 2005/0049470 A1 | 3/2005 | Terry | |
| 2006/0081259 A1 | 4/2006 | Bruggeman et al. | |
| 2006/0155172 A1* | 7/2006 | Rugg | A61B 5/1113 600/300 |
| 2007/0056582 A1 | 3/2007 | Wood | |
| 2008/0228045 A1 | 9/2008 | Gao et al. | |
| 2009/0118598 A1* | 5/2009 | Hoarau | A61B 5/14552 600/301 |
| 2012/0277548 A1 | 11/2012 | Burton | |
| 2012/0310669 A1* | 12/2012 | Carlberg | G06F 19/322 705/3 |

\* cited by examiner

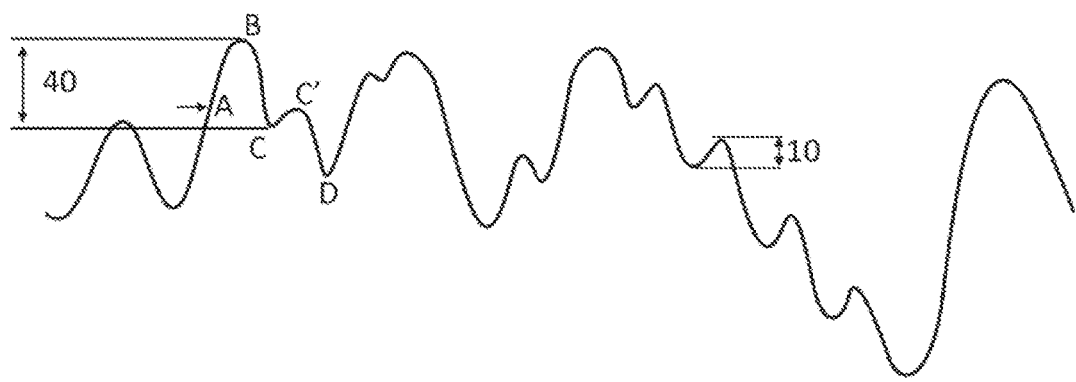
FIG. 4
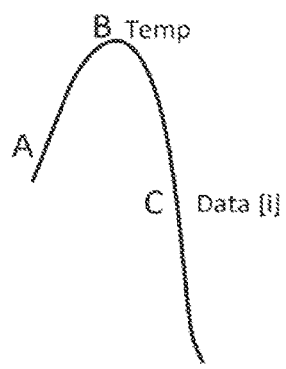 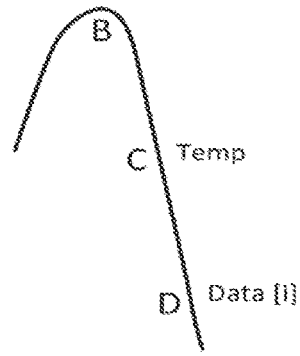
FIG. 5A	FIG. 5B

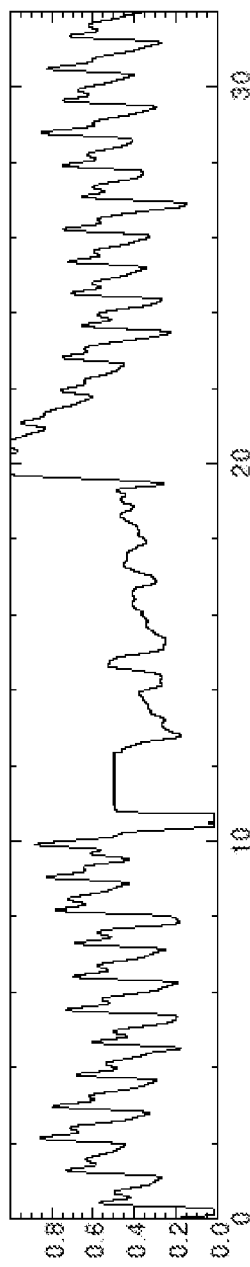
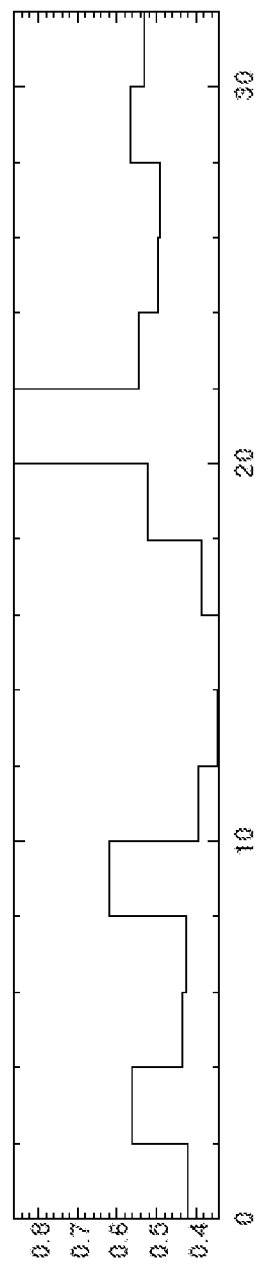
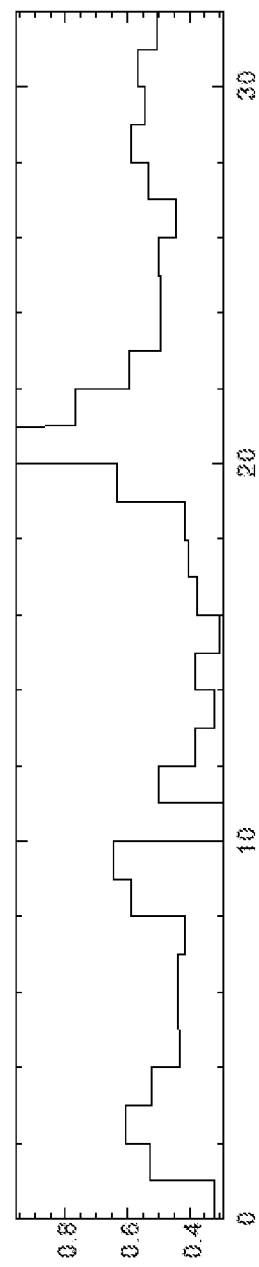
FIG. 7A
FIG. 7B
FIG. 7C

PATIENT IN-THE-LOOP PARTICIPATORY CARE AND MONITORING

CROSS-REFERENCE TO RELATED APPLICATIONS

This application is the U.S. national stage application of International Application Serial No. PCT/US2013/041590, filed May 17, 2013, which claims the benefit of U.S. Provisional Application Ser. No. 61/649,165, filed May 18, 2012, which are hereby incorporated by reference in their entirety, including all figures, tables and drawings.

BACKGROUND

Currently, many healthcare assessments and interventions require the presence or active involvement and/or the diligence or attention of a clinician. Examples include the assessment of consciousness or lack thereof (whether a patient responds or does not respond to a non-noxious stimulus) and the assessment and documentation of patient comfort or pain score. Other examples include an intervention involving a request to bed-ridden patients to periodically take a deep breath to improve lung status and the intervention involving a request to bed-ridden patients to periodically shift their weight to prevent pressure sores.

A clinician may also be called upon to respond to alarm conditions of patient monitors in situations where the alarm is a result of a patient moving too much or positioned in a manner that obstructs a reading or creates a kink in tubing. These types of alarms may occur as high as 700 times per patient per day in some settings leading to "alarm fatigue" due to being called in to, for example, ask a patient to move less to eliminate/reduce motion artifacts during electrocardiography (ECG) or pulse oximetry or adjust their position to remove a kink or other obstruction in intravenous (IV) tubing.

Providing general hospital and pain management care, as well as pressure sore prevention and other quality of care metrics are deemed important in the healthcare environment. In cases where a healthcare worker or provider may not be or is suspected not to be compliant with patient care guidelines, such as providing sponge baths on a periodic basis, the patient can be asked as a quality control measure if a sponge bath was given. Similarly, consciousness monitoring during conscious sedation is currently performed by a clinician engaging in idle chit chat with the patient to verify that the patient is conscious.

As one example, the consciousness of a patient is an important factor for administering sedation as well as for monitoring head injuries. Typically, as a first assessment of consciousness, a patient's verbal response or actions in response to a query or prompt is used to indicate whether the patient is awake and conscious. However, when a patient is immobilized or cannot verbally communicate due, for example, to intubation, or the patient being mute or for unimpaired patients, a clinician being absent or otherwise preoccupied, other means are needed to assess the patient's care including consciousness.

Current systems for determining consciousness of a patient provide a switch or button for a patient to depress in response to a query or prompt. For example, if the patient is awake and conscious, the patient presses the button or toggles a switch in response to the query or prompt, thereby communicating consciousness. If no button press or switch toggle is registered within a set time period from the query or prompt, the patient is presumed to be unconscious.

BRIEF SUMMARY

Methods and systems are disclosed herein for enhancing patient care and patient safety by empowering patients—and even heath care devices—with the means to communicate and contribute to patient care, surveillance, monitoring, and reduction in alarm frequency in a variety of healthcare settings. In accordance with various embodiments, methods and systems for monitoring consciousness of a patient during sedation, pain management, and other monitoring and patient care modalities are provided.

Various methods and systems are further provided for enabling communication between a caregiver or the caregiver environment (including a monitor or other device) and the patient. Applicable scenarios include when the patient is not able to speak or has limited motion capabilities or when a clinician or healthcare worker is not physically present or too preoccupied to provide the prompt, assessment, instruction or care.

In certain embodiments, induced or reduced motion, perfusion or other artifacts or artifact manipulation in an oximeter probe signal are detected and analyzed to determine whether a patient is responding to a query or prompt. According to one method, a patient is provided with a pulse oximeter probe, typically on a finger (but embodiments can also be implemented where the probe is on a toe, nasal septum or other body part). The output of the pulse oximeter probe is monitored and analyzed to determine the patient's response to a query or prompt. Thus, in various embodiments, in addition to using the oximeter to monitor the oxygenation and pulse of the patient, the oximeter is used as part of a patient-in-the-loop system in which the patient can communicate a response or initiate an action to a periodic, contextual, timed or other query or instruction that may include a menu of choices and therapy instructions (such as take a deep breath, wiggle your finger three times if your pain score is greater than x, shift your weight to prevent pressure sores, keep your finger still, straighten your arm, move your leg(s), etc.). Monitoring a patient's perceived pain score is part of the Surgical Care Improvement Project (SCIP) measures to monitor quality of care and compare or benchmark how different institutions rate compared to each other.

For example, a patient can be prompted (by a person or monitor or other healthcare environment device) to squeeze or press his or her finger where the pulse oximeter probe is placed against one or more other fingers or surface such that the vascular bed inside the pulse oximeter is depressed or squeezed, leading to artifacts (in this case a perfusion artifact) in the photoplethysmogram (the analog waveform indicating the output from a photodetector that is part of a pulse oximeter probe).

In another example, the patient can be prompted (by a person or monitor or other healthcare environment device) to wiggle or shake the finger (creating a command-time-linked motion artifact) having the pulse oximeter probe. The squeezing or deliberate shaking or other artifact manipulation by the patient can also be used to indicate a response to a query (e.g., to provide a "yes" answer or a "no" answer to a question or to pick an answer or response from a menu of more than two choices).

The motion and/or perfusion artifacts created in the oximeter output signal due to the shaking or squeezing by the patient and the temporal relationship to the prompt/query are used to determine the patient's response or lack thereof.

A system is provided that determines consciousness and/or a non-verbal response of a patient according to a deliberately induced artifact in a pulse oximeter probe. In one embodiment, the system specifically detects changes (e.g., the signal degradation or other artifact manipulation) in an output signal of an oximeter caused by the patient squeezing the oximeter probe (or shaking a finger on which the oximeter probe is placed) shortly after the patient is prompted to do so.

In one embodiment, a patient is prompted to shake the finger on which the oximeter probe is placed. In another embodiment, the patient can be prompted to squeeze the finger having the oximeter probe against the opposing thumb, another finger and/or another surface. The finger squeeze can be sustained or the finger squeeze can be a series of squeezes where the number of squeezes corresponds, for example, to the number in a menu or a pain score. The intentional shaking or squeezing deliberately injects or manipulates an artifact into the oximeter output. The artifacts in the oximeter output are used to determine whether the patient responded (and is conscious) and for other functions such as confirming that the patient has understood the instruction or indicating that the patient does not understand the instruction: "squeeze once if you understand the instruction; if you did not understand the instruction, squeeze twice". For cyclic motion, peak detection can be used to determine the response. Other embodiments can utilize Fourier transforms, wavelets and/or pattern recognition and/or feature extraction algorithms. A "conversation" (including patient responses) may be carried out with the patient using libraries of queries, instruction, prompts and responses.

It should be understood that while the above examples incorporate a pulse oximeter, embodiments are not limited to the pulse oximeter and other patient sensors or devices, including, but not limited to, a patient bed, infusion pump, Patient Controlled Analgesia (PCA) pump, blood pressure monitor, ECG, capnometer, capnograph, calf compression device, and a nurse call system, are contemplated within the scope of the invention.

For example, in certain embodiments, a PCA pump button may be used to indicate a patient response to a query or prompt. Thus, in various embodiments, in addition to using the PCA pump to enable a patient to control the administration of analgesia, the PCA pump is used as part of a patient-in-the-loop system.

In some embodiments, monitoring devices can utilize a patient-in-the-loop approach to enable self-correction for alarms. A monitoring device (or other device) may sense an impending condition and instruct, as a first resort, the patient to make a self-corrective maneuver. Certain alarm conditions can be corrected and/or addressed by outputting at the monitoring device or some other healthcare environment device to which the monitoring device can communicate with, an alarm or request to a patient to respond to instructions such as take a deep breath, shift your weight, keep your finger still, straighten your arm, move your leg(s), and the like.

This Brief Summary is provided to introduce a selection of concepts in a simplified form that are further described below in the Detailed Description. This Brief Summary is not intended to identify key features or essential features of the claimed subject matter, nor is it intended to be used to limit the scope of the claimed subject matter.

BRIEF DESCRIPTION OF THE DRAWINGS

FIG. 4 shows an example photoplethysmogram of data acquired in accordance with an embodiment of the invention.

FIGS. 5A and 5B respectively illustrate uphill and downhill curves formed by acquired data points for explaining a peak detection method used in an embodiment of the invention.

FIGS. 6A-6C and 7A-7C show plots for explaining a discrete wavelet transform method used in an embodiment of the invention.

FIG. 8A shows a plethysmogram with no artifact, indicating no action by a patient; FIG. 8B shows a plethysmogram when a patient is squeezing the finger with the oximeter probe repeatedly. The squeezing is cyclic (not constant); each hump corresponds to a squeeze and release of the finger; and FIG. 8C shows a plethysmogram when a patient is shaking the oximeter. The induced artifact either appears or disappears following the prompt and the change in the plethysmogram waveform (ac and/or dc signal) is temporally linked to the prompt.

FIG. 13A shows the back panel of a Nellcor™ pulse oximeter monitor; FIG. 13B shows the wrapper for the Nellcor™ Neonatal-Adult Pulse Oximeter Probe used for the experiments; FIG. 13C shows a front view of the Nellcor™ pulse oximeter monitor; FIG. 13D shows an ACCESS I/O data acquisition board; and FIG. 13E shows the test set-up.

DETAILED DISCLOSURE

Figure 1:
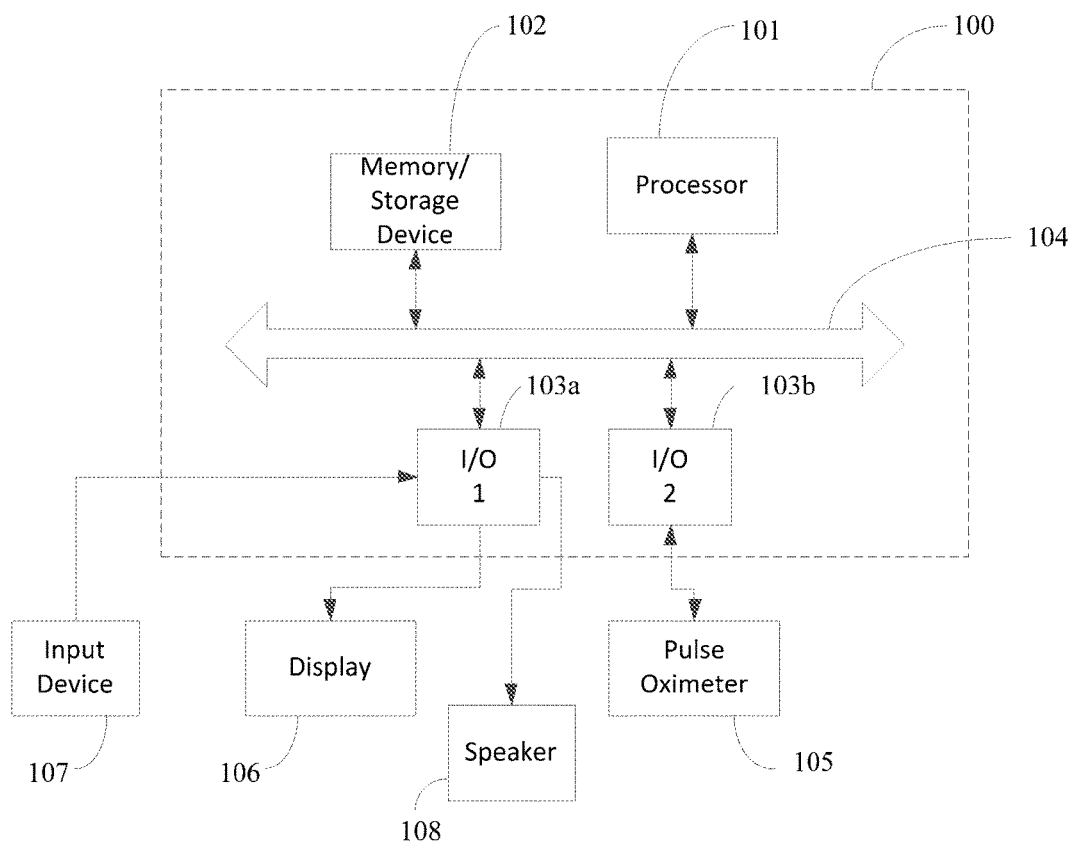
FIG. 1 illustrates a system for consciousness monitoring in accordance with an embodiment of the invention.

Methods and systems are disclosed herein that involve a patient in-the-loop approach, enabling a patient to deliberately provide input or respond to instructions as part of a monitoring system for applications including consciousness monitoring during sedation, pain management and other monitoring and patient care modalities.

In addition to consciousness monitoring, pain management, quality control and monitoring such as SCIP measures, various implementations are suitable for care and monitoring applications including, but not limited to, respiratory care, ECG monitoring, capnography, alarm prevention/management/reduction such as for infusion pumps, pressure sore prevention, incentive spirometry, and deep vein thrombosis prevention.

Furthermore, data derived from these patient-in-the-loop techniques can be formatted to be received and interpreted by electronic medical record (EMR) and electronic record keeping systems. Example EMR and electronic record keeping systems include solutions available from Epic Systems Corp. and Recordkeepers, Inc as well as OpenEMR available under a GNU General Public License.

The systems described herein can include interfaces for available EMR and electronic record keeping systems so that results from a patient-in-the-loop response can be recorded. In some cases, data collected and/or analyzed by the described systems can be formatted and inserted or transmitted for recording as part of an electronic record.

Embodiments of the invention use action artifacts or cessation thereof in a pulse oximeter signal caused by deliberate action of a patient as an indicator of a response to a patient query. According to an embodiment, the output signal of a pulse oximeter is analyzed for induced or terminated artifacts representing a response to verbal commands.

Pulse oximetry, via a medical device referred to as a pulse oximeter, detects blood pulsation and oxygen in the blood using a non-invasive light transmittance approach where red and infrared light are alternately directed through a thin vascular bed of a patient to a photodetector. The absorption of the red and infrared light as it passes through the patient to the photodetector is used to indicate oxygenation of the blood. Accordingly, the amount of light detected at the photodetector can be used to calculate the amount (e.g., ratio) of oxygen in the blood, as well as the patient's pulse and other physiological characteristics. Pulse oximeters use several wavelengths of light, including red and infrared, because the absorption of the red and infrared wavelengths in the presence of oxygenated hemoglobin (oxyhemoglobin) and hemoglobin (deoxyhemoglobin) are significantly different. The ratio of the absorption of the red and infrared light can be used to calculate the oxygenation of the blood (e.g., ratio of oxyhemoglobin to deoxyhemoglobin). The output of a pulse oximeter can be used to provide a photoplethysmogram (PPG) for display on a monitor, enabling healthcare professionals (and others) to obtain a visual indication of the patient's oxygenation (and heart rate).

During pulse oximetry monitoring, artifacts in the signal due to noise in the signal path as well as voluntary and involuntary patient movement are typically removed electronically in order to obtain a more accurate display and calculation of the oxygenation of the patient's blood and the patient's heart rate measurement. In addition to using the monitor or another device to prompt the patient to remove artifacts from the pulse oximeter's output signal, certain embodiments of the invention also take advantage of induced artifacts in the signal to determine a patient's consciousness and/or response to a query or prompt.

Pulse oximeters are quasi-omnipresent in the healthcare setting. Thus embodiments provide an in-the-loop approach for patients without needing another device (beyond the devices and connections already in the patient's immediate environment being used to monitor and perform a medical function) for the patient to use. The ability to function without an additional sensor or device can be particularly useful in areas where a query response handgrip is not used or not previously contemplated for use.

In addition to pulse oximeters, other embodiments of the invention utilize other monitors of patient physiological parameters by taking into consideration artifacts in the monitors' signals caused by deliberate action of a patient as an indicator of a response to a patient query. Thus, these other existing monitors, sensors or devices, including, but not limited to, electronic beds, infusion pumps, blood pressure monitors, ECGs, capnometers, capnographs, PCA pumps, calf compression devices, and nurse call systems, provide other means for patient-in-the-loop participatory care and/or monitoring where pulse oximeters are not used but where the other existing monitors are in common use.

In accordance with various embodiments of the invention, the patient's response to a question can be detected through, for example, using a pulse oximeter without the need for an additional sensor. The induced or terminated artifacts in the pulse oximeter signal are used as part of the patient in-the-loop participatory monitor. A regular pulse oximeter sensor can be used without any modifications as was done with the working model. Instead of modifying existing pulse oximeter probes, a software module/upgrade can be added to a pulse oximeter's software in order to produce and interpret the signal artifacts to provide patient feedback and enable a determination of patient consciousness when a patient is unable to move or speak or a clinician is absent or otherwise engaged.

In a further embodiment, an interface is provided to produce the query prompt via one or more of the five senses, depending on whether the patient is healthy, deaf, mute, or impaired in some manner. For example for an audible prompt, earbud speakers, headphones or direct broadcast speakers (already incorporated into most monitors and/or at patient care locations) among others may be used to deliver the prompt/query/instruction. For a visual prompt, a display can provide written prompts or instructions (in the appropriate language) or graphical/iconic instructions. For a tactile prompt, in one embodiment, a non-invasive blood pressure cuff can be inflated or pulsated in a way that distinguishes the cuff manipulation indicating a prompt from the regular cuff inflation or some other tactile stimulus could be used. For example, a pain or electrical stimulus may be delivered by a nerve stimulator (and which may already be present in the healthcare environment of the patient).

According to certain embodiments, a system is provided that determines consciousness and/or a non-verbal response of a patient according to a deliberately induced artifact in a pulse oximeter probe signal. In one embodiment, the system specifically detects changes in an output signal of an oximeter caused by the patient squeezing the oximeter (or shaking a finger on which the oximeter is placed) shortly after the patient is prompted to make or terminate a particular deliberate motion.

FIG. 1 illustrates a system for consciousness monitoring in accordance with an embodiment of the invention. Referring to FIG. 1, the system 100 can have hardware including one or more computer processing units (CPUs) 101, memory and/or mass storage (e.g., hard drive) 102, and I/O ports 103a, 103b. Elements of the computer system hardware can communicate with each other via a bus 104. The I/O ports can include various connectors suitable for connecting various devices for communication with the system 100. Although I/O port 1 103a is shown as a single interface, it should be understood that multiple I/O ports may be available. For example, I/O port 2 103b can be provided for connecting a pulse oximeter 105 to the system 100. Other devices that can connect to an I/O port include, but are not limited to a display 106, an input device 107, and a speaker 108. The display can be provided for displaying a graphical interface output from the system. The input device 107 can be any suitable input device for enabling a user to interact with or input data to the system 100. For example, the input device 107 can be a programming interface or a mouse or keyboard. The speaker 108 can be provided in the form of a speaker already existing in the monitor, a headset, earbuds or broadcast speakers.

According to various embodiments, computer-readable instructions for performing a patient in-the-loop consciousness assessment can be stored in the storage device 102 and accessed for execution by the processor 101. Processing modules for execution by the processor 101 can be provided to read data received from the pulse oximeter 105 via the I/O port 2 103b; store the received data at a location in the memory or storage device 102; and analyze the stored data to determine patient consciousness (or other particular response). Additional processing modules can be provided to enable display of the captured (received) data and results of the analysis. In addition, voice samples and/or other sounds or visual, tactile or other cues may be stored in the system 100 for output through the speaker 108 or another device via an I/O port.

In a further embodiment, an initial set up for the system includes a learning phase for establishing specific baseline measures, which can provide additional robustness to the system. For example, no-motion data points and deliberate motion or squeeze data points can be established during the learning phase. The no-motion data points can be taken for a predetermined period of time. Similarly the deliberate motion or squeeze data points can be taken for one or more deliberate actions. The one or more deliberate actions can include, but are not limited to, shaking a finger (having the oximeter probe) for a period of time or a particular number of times, alternatingly squeezing and releasing the finger (having the oximeter probe) for a period of time or a particular number of times, and tapping the finger (having the oximeter probe) for a period of time or a particular number of times.

The deliberate artifact data points collection can be aided by using an automated speaker. For example, the patient can be asked to shake her finger for a sustained period (e.g., 10 seconds or more) by outputting a sound or tone for the sustained period of time. The instructions can be given in person or by a recording stating, for example, "shake your finger and keep shaking it as long as a tone that will follow is sounding."

In one application, the artifacts or lack of artifacts in the output signal of a patient's pulse oximeter are assessed to determine the loss of a patient's response to verbal commands. The existence of interactive, system-inducible artifacts in the signal indicates a responsive patient (who is considered to be conscious). However, the degradation (as in longer time delay or a trend towards longer time delays between the query and the response) or absence of response can be used as a precursor and early warning of unconsciousness and apnea.

In accordance with certain embodiments of the invention, a patient is involved with his or her own monitoring for a variety of monitoring modalities. For example, a patient can be asked to take a deep breath or hold his or her breath and then provide confirmation that the requested action was performed. A confirmation may be obtained via another device (e.g. a capnograph) as well as by pulse oximetry.

In another application, the subject system can use the pulse oximeter as a nurse call button. In one embodiment, the patient can perform a particular deliberate motion to indicate that a nurse is being requested. For example, a patient can shake her finger in 3 quick bursts to call a nurse. In such embodiments, the output of the data analysis can be sent to a nurse station over a network such as a Hospital Information System (where the system includes a network interface). In addition, or as an alternative, an alarm can be sounded. Using the oximeter (or other device configured as part of a patient-in-the-loop system) as a potential nurse call button can be handy when the nurse call button is inaccessible by the patient or lost in the bed sheets.

In yet another application, the artifacts in the output signal can provide pain score documentation. For example, the pulse oximeter can announce "Please tell us your pain score on a level of 1 to 10. We will slowly count from 1 to 10. When we say the number that is your perceived pain score, shake your finger" or alternatively "Squeeze your finger the same number of times as your perceived pain score" and the pain score level is then automatically recorded at periodic intervals with no or minimal clinician time expenditure. In one embodiment, a tactile prompt using a non-invasive blood pressure cuff can be part of a tourniquet pain test in which pain scores (and thus the effect of sedatives/analgesics) can be obtained via the deliberate inducement of artifacts in the oximeter output signal as the blood pressure cuff is used to create pain. In yet another embodiment, a blood pressure cuff on the same arm as the oximeter probe could be inflated during the time that the patient is being queried. The cuff will cut off circulation and, thus, also the cardiac pulse, providing a cleaner signal (compared to when the cuff is not inflated). Against this temporary cleaner backdrop, the induced artifacts can be more readily detected.

Figure 2:
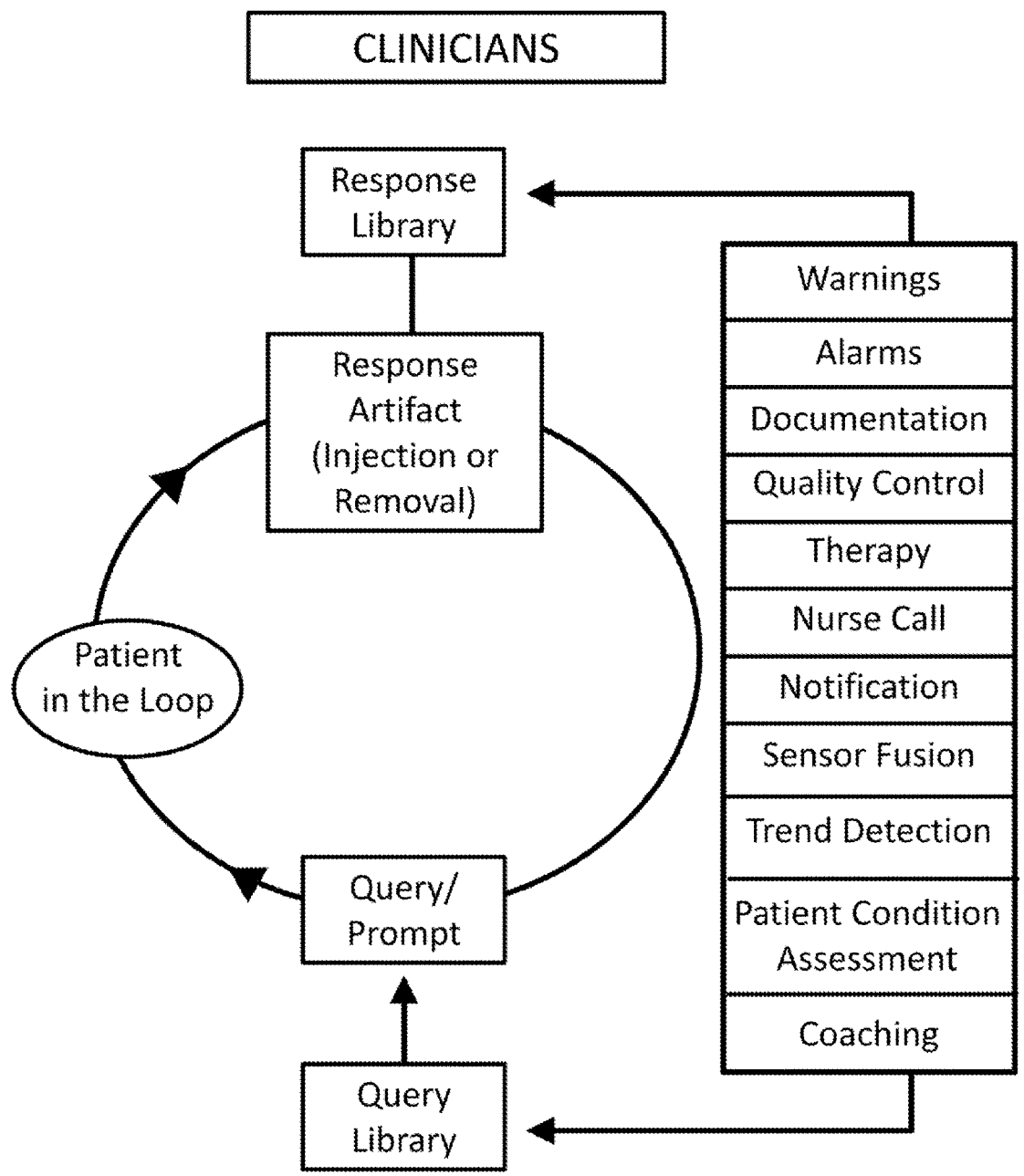
FIG. 2 shows a diagram of a patient in-the-loop system in accordance with various embodiments of the invention.

FIG. 2 shows a basic diagram of a patient in-the-loop system in accordance with various embodiments of the invention. The system enables a two way "conversation" between the patient (who is in the loop) and the system by outputting a signal and causing a patient to use one or more of the five senses (hearing/audio, sight/visual, touch/temperature, smell, taste). The system can include a library of prompts (e.g., audio prompts) and a library of responses indicative of deliberate manipulation of artifacts (motion, breath holding, hyperventilation, facial expressions such as squinting and frowning when using BIS or EEG pads/leads, etc.) to hold the two-way "conversation" between the monitor/system and the patient where the term "conversation", including in the figures, encompasses any kind of interaction with the patient.

One or more of warnings, alarms, documentation, quality control, therapy, nurse call, notification, sensor fusion, trend detection, patient condition assessment, and coaching can direct the query or prompt to the user and provide the particular response library upon receipt and interpretation of the response from the patient in-the-loop.

Examples of the above warnings, alarms, documentation, quality control, therapy, nurse call, notification, sensor fusion, trend detection, patient condition assessment, and coaching are provided as follows and should not be construed as being limiting.

For example, a warning can be issued when a patient needs a second prompt to respond or there is a trend towards longer response times during consciousness monitoring. An alarm can be sounded where a patient is not responsive to verbal commands during consciousness monitoring. Automatically querying and recording the pain score at prescribed intervals is an example of documentation.

An example of quality control is when an unintended motion artifact is detected and the patient is asked to keep the hand still and the artifacts disappear, confirming that this was not a sensor defect. Another example of quality control is where a PPG signal and/or a $SpO_2$ value is at or around 85, indicating that the probe has fallen off or is misplaced. In such an event, a prompt can be made to the patient to place the pulse oximeter back on the finger and an output provided to the patient (such as "well done") when the signal re-appears and the data indicates that the probe has been successfully reinstalled.

An example of therapy is to periodically instruct the patient to take a deep breath or to shift one's weight. The nurse call can provide a request for a nurse. An example of notification and of patient condition assessment is the clinician being notified that the patient is cold based on automatic query and confirmation. A trend towards an increase in patient reported pain score can be flagged and reported. An example of coaching is the detection of a less than optimal breath when asked to take a deep breath and the patient being coached to take a deeper breath or trained over time to develop larger chest expansions.

In an example implementation, the library can include queries including asking a patient whether he is ready to be extubated. For example, the prompt/query can be triggered by the detection of a motion artifact from the pulse oximeter that indicates the patient is waking up or restless. As part of confirming whether the patient is truly ready to be extubated, the query library can be used to ask the questions typically asked by clinicians such as "What day is it? Shake your finger (or introduce other recognizable artifact) when we say the right day. Monday <pause> Tuesday <pause> Wednesday <pause> Thursday <pause> Friday <pause> Saturday <pause> Sunday. Or a simple math problem such as adding two single numbers might be asked and afterwards a set of "answers" containing the right answer is slowly enunciated.

Once a response by the patient indicating a successful selection of the day and/or solution to the math problem or other question is received (and determined from the signal), the clinician can be alerted that the patient has correctly answered the questions indicating he is conscious.

A head lift sustained for 5 seconds or its equivalent may also be requested by the query library and the ability to the patient to perform the action detected by artifacts introduced from the head lift or equivalent (such as raising for 5 seconds the arm with the blood pressure cuff or the hand with the pulse oximeter probe which will introduce recognizable artifacts that can be detected by signal analysis).

According to certain embodiments of the invention, the patient manipulates deliberate artifacts via a pulse oximeter. In further embodiments of the invention, the patient can deliberately "delete" artifacts by stopping motion. For example, if the system (or a user of the system) determines that the signal is suspicious, the patient can be requested to stop moving the hand having the pulse oximeter probe or the probe can be shielded from bright light or replugged.

Figure 3A:
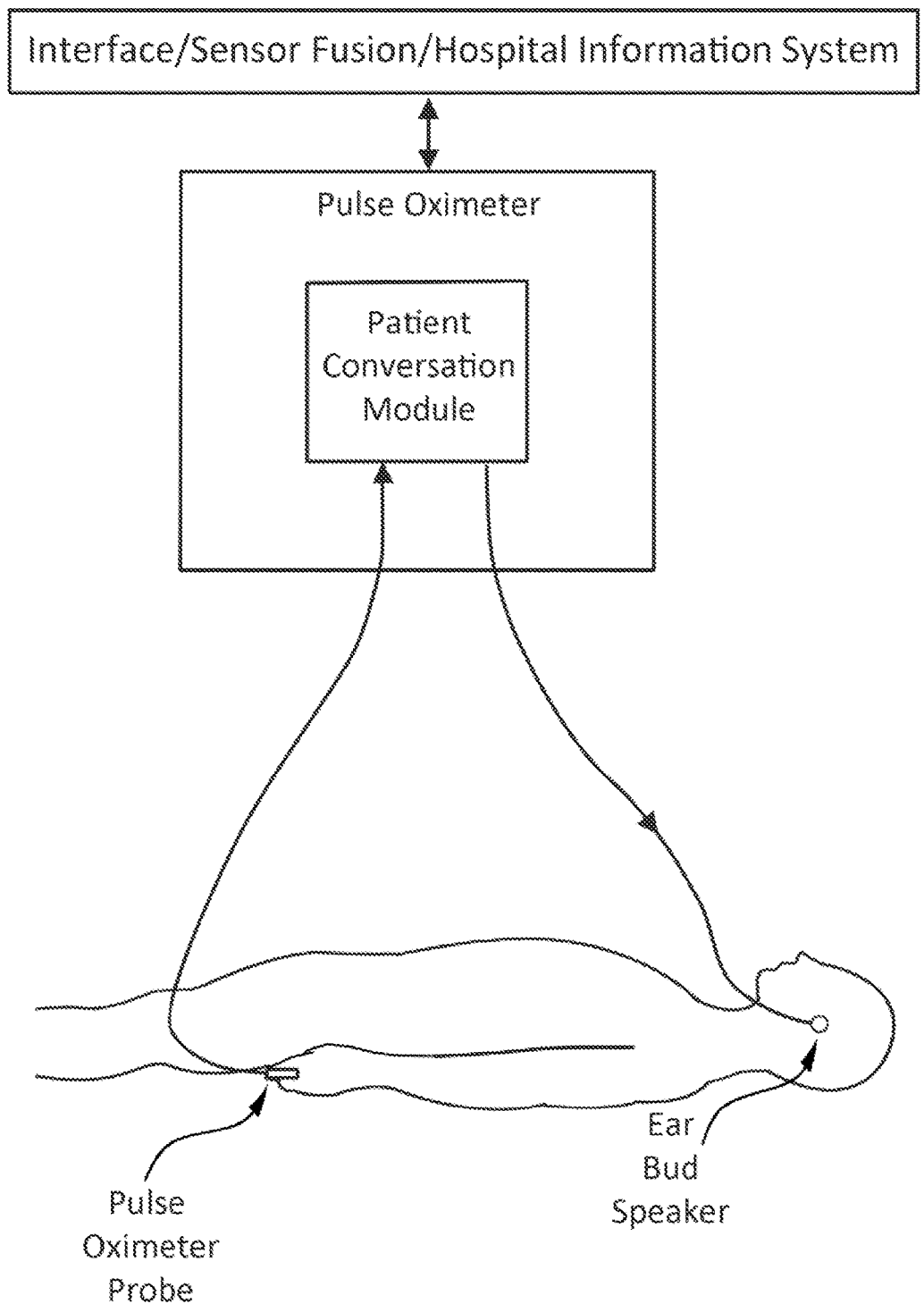
FIG. 3A shows a diagram of an implementation of a patient-in-the-loop system in accordance with an embodiment of the invention.

FIG. 3A illustrates a diagram of an implementation of a patient-in-the-loop system in accordance with an embodiment of the invention. The Patient Conversation Module functions to enable the patient interaction. The Patient Conversation Module can be implemented as hardware, software, or a combination of hardware and software that is integrated with or separate from the existing monitors.

Figure 3B:
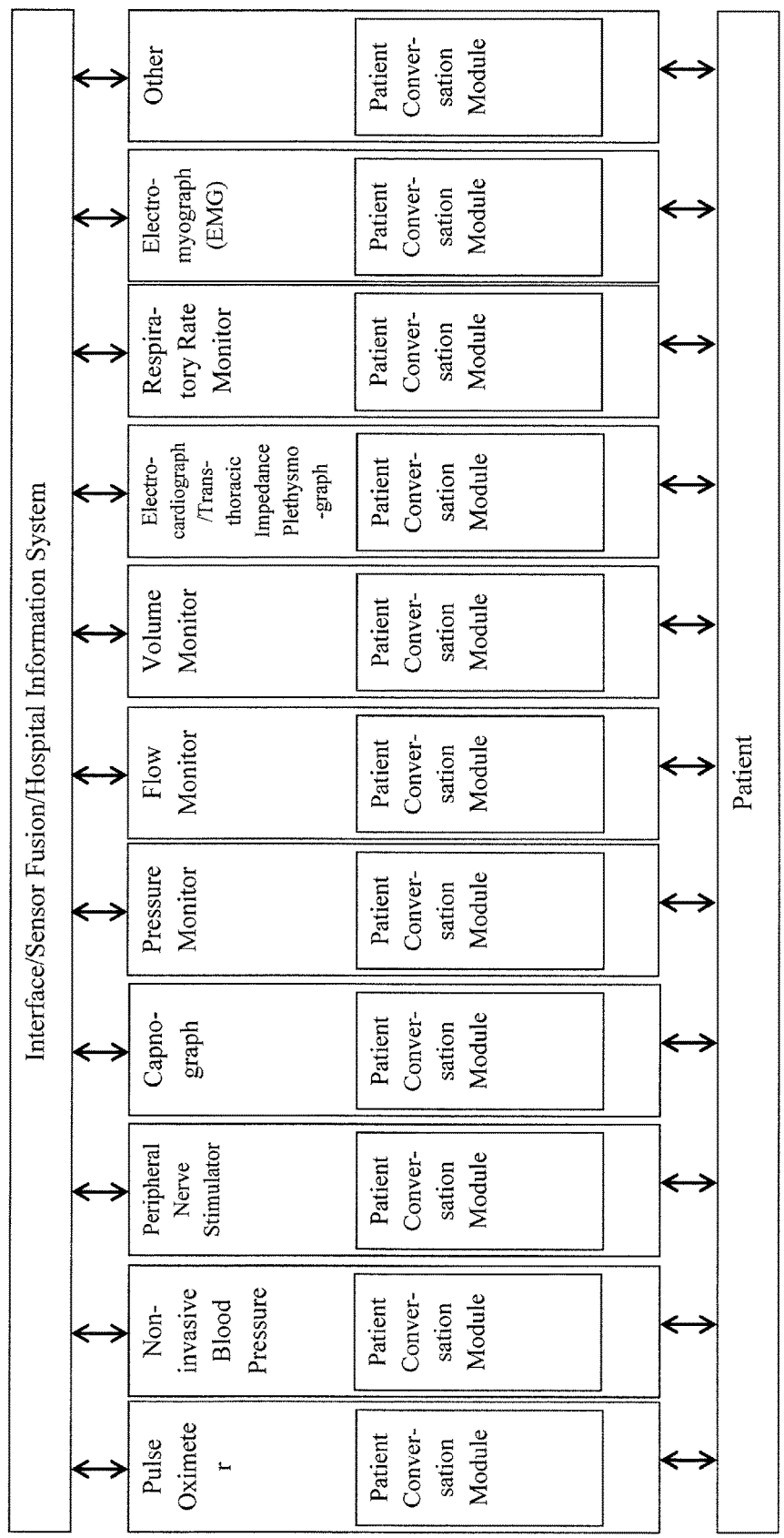
FIG. 3B shows a diagram of a monitoring system with enhanced monitoring equipment in accordance with various implementations that are contemplated in accordance with embodiments of the invention.

FIG. 3B illustrates various implementations that are contemplated in accordance with embodiments of the invention. As shown in FIG. 3B, a patient conversation module can be integrated internally or externally with one or more existing monitors (e.g., one or more of a pulse oximeter, non-invasive blood pressure monitor (NIBP), peripheral nerve stimulator, capnograph, pressure monitor, flow monitor, volume monitor, electrocardiograph/transthoracic impedance plethysmograph, respiratory rate monitor, electromyograph (EMG), and/or some other monitor) and communicated to a caretaker, clinician or other provider via an interface, sensor fusion or hospital information system along with the output of the existing monitor.

Sensor fusion refers to embodiments where data or an artifact reported by one sensor A (such as pulse/heart rate in pulse oximeter) is confirmed by at least another independent sensor B (for example ECG) or sensor C (for example NIBP) using preferably another measurement principle) to confirm a measurement/artifact. Sensor fusion enables a higher level of confidence that the prompted artifacts (in response to prompts/queries/instructions are in fact the artifacts being sought and not actually random artifacts (false positives or false negatives).

Various pulse oximeter implementations have already been described. According to an embodiment using a blood pressure cuff (e.g, NIBP), deliberate tapping or squeezing by the patient can be used. In the blood pressure cuff implementation, the cuff tap and cuff squeeze can be carried out in a similar fashion as described with respect to the pulse oximeter implementation. As seen in FIGS. 9A-9B and 10-10B, the morphology of the waveforms corresponding to the taps and the squeezes are distinctly different. The tap produces a sharper spike-like bump whereas the squeeze produces a more rounded bump. This distinctive shape between taps and squeezes could be used in an analogous way as dots and dashes in a telegraphic code.

In one implementation, a controller for the NIBP is configured to place the NIBP machine on venipuncture setting during a query response. When in venipuncture setting, the cuff pressure will be constant if unperturbed and there will be no artifacts in terms of pressure changes or oscillations from an actual NIBP blood pressure measurement cycle to deal with during a query response. Thus perturbations during the query response cycle that occur within an allowed time window after a query may be interpreted with a higher degree of confidence as responses from the patient.

A capnograph (for carbon dioxide monitoring) can be used in place of (or in addition to) a pulse oximeter. For example, whether intubated or with nasal cannula sampling, a patient can be requested to "give a series of short exhalations or hold your breath or give a very long and slow exhalation." The number of short exhalations will show up as the same number of small bumps instead of one large bump for a regular exhalation. That is, the patient can be requested to exhale in patterns that can be uniquely interpreted Another implementation is a peripheral nerve stimulator with inbuilt accelerometer (such as the TOF Watch used at UF&Shands). While there is no electrical stimulation, the patient can be prompted to move or shake or contract or twitch or frown a thumb or other body part (such as facial muscles) on which the accelerometer is attached in patterns that can be uniquely interpreted.

For the pressure monitoring implementation, an intubated patient, e.g., in the intensive care unit (ICU), can be asked to tighten the chest muscles to make the thorax compliance stiffer resulting in a higher pressure than baseline inspiratory pressure during inhalation; or asked to take a deep breath or series of small breaths with resulting pressure dips and detect and interpret the response by unique patterns in airway pressure.

For the flow monitoring, an intubated patient, e.g., in the ICU, during exhalation, can be asked to pause (stop exhaling and then resume exhaling) a few times so that the exhaled flow rate drops to zero or dips in unique patterns that can be interpreted.

For the volume monitoring, the patient can be asked to do a larger exhalation than usual or to do multiple small exhalations or to temporarily withhold expiration or other patterns that can be uniquely interpreted.

For the respiratory rate monitoring, the patient can be asked to temporarily hyperventilate or hypoventilate or breath hold-in patterns that can be uniquely interpreted.

For the electrocardiograph (ECG), the patient can be requested to, for example, wiggle or remove an ECG lead as a response. Alternatively, transthoracic plethysmography (TTP) can use the electrical impedance across the thorax (measured via the ECG pads/leads) to infer respiratory effort and a query/prompt to take a deep breath could be confirmed by ECG/TTP (as well as pulse oximetry).

For the electromyograph (EMG), the patient can be asked to twitch, contract or frown at body locations where the EMG sensor is placed to create artifacts on the EMG signal in unique patterns that can be interpreted.

The input, output or probes attached to the patient can be wired or wireless.

In another embodiment, a PCA pump may be incorporated in place of or in addition to a monitoring device. For example, in certain embodiments, a PCA pump button may be used to indicate a patient response to a query or prompt. The PCA pump button is generally used (e.g., pressed) by a patient whenever the patient feels pain so that pain medication is delivered at the patient's command. In addition to, or in place of, detecting a response by inferring motion or squeezes or artifacts in a signal, a direct response can be provided by the use of the PCA pump button.

According to an implementation, the pump can be configured to switch modes of operation so that a patient's use of a button associated with the pump during a prompted "response" does not cause analgesic to be dispensed.

In one scenario, the PCA pump processor can be configured to ask the patient after receiving an indication that the patient has self-administered a PCA bolus (after an appropriate wait time based on PK/PD) about the perceived pain score using a response system designed to work with the PCA pump.

In another scenario, the PCA pump can be used with integrated monitoring equipment such as a pulse oximeter with patient-in-the-loop participatory care and monitoring where the processor for the PCA pump is configured to use a first button push for participatory feedback and a subsequent button push for administration of a PCA bolus. For example, a PCA button push may first trigger an audio prompt to document the perceived pain score and then when the score has been entered by the patient deliver the PCA bolus based on the pain score. In some cases, where no response is provided for a certain elapsed time, a determination may be made that the patient is unconscious (and no analgesic is delivered).

A comparison of the pre- and post-"PCA button push" pain scores may be performed in some cases to deduce ratios between PCA requests, PCA deliveries and successful PCA administrations (those PCS administrations resulting in a subsequent decrease in pain score).

Thus, in various embodiments, in addition to using the PCA pump to enable a patient to control the administration of analgesia, the PCA pump is used as part of a patient-in-the-loop system.

In order to confirm an existence of an artifact and/or improve signal quality, if an unprompted artifact is detected, the system can instruct the patient to "Please stop shaking your finger or moving your hand or arm" or "Please remain still". If the motion artifact then disappears, this confirms that the signal disruption was due to motion artifact or the patient being cold and shivering. Based on the plethysmogram for the oximeter output, additional information can be obtained. For example, by analyzing signal strength, some inferences may be made to the condition of the patient. In one embodiment, the PPG signal strength can be analyzed to determine whether there is reduced perfusion due to vasoconstriction and the patient can be asked "if you are cold, shake your finger in 4 short bursts." If a positive response is provided by the patient (in combination with a determination that there is vasoconstriction), then a message can be provided to the patient's caregiver (medical or nonmedical) that the patient needs warming. Similarly, a combination of patient response (via artifacts in the pulse oximeter) and sensor outputs (from the pulse oximeter or other sensor device being used to monitor the patient) can be used to assess and address a variety of the patient's needs.

In a further embodiment, the query response can be used as a quality assurance signal and/or as synergy for extracting the respiratory rate from a photoplethysmogram of the oximeter output by determining the low frequency oscillations in the PPG signal that corresponds to respiration as opposed to the higher frequency oscillations related to the cardiac pulse. For example, if the query response is indicative that the patient is unresponsive or that there is a trend towards longer lag times before the patient responds to a query, then the algorithm extracting the respiratory rate can be made more sensitive as there is an impending likelihood of apnea developing. If the query response indicates all is fine, a less sensitive respiratory rate extraction algorithm may be used that provides less false alarms.

Embodiments of the invention use artifact detection to determine whether a patient is providing feedback. In one embodiment, consciousness monitoring is carried out by searching for the number of peaks in a time interval or a set number of samples. Motion can be inferred if the number of peaks has increased from the number of peaks found in the signal before motion was prompted. In another embodiment, pattern recognition is used. In yet another embodiment Fourier transform algorithms, Fast Fourier Transform (FFT) algorithms or wavelets are used.

In one embodiment, the motion artifact detection involves searching for the large peaks (beyond those caused by the cardiac pulse) that are added by finger shaking (motion artifact) to the analog photoplethysmogram data acquired by the system and discards the small peaks caused by noise. FIG. 4 shows an example photoplethysmogram of data acquired in accordance with an embodiment of the invention. To discard small peaks caused by noise, threshold values can be established. For example, if the height of the peak is greater than 10 mV while rising up AND greater than 40 mV while going down (see FIG. 4), then it is counted as a peak otherwise it is considered as noise. It should be understood that the 10 mV and 40 mV thresholds are programmable or learned via artificial intelligence and can be set and adjusted as desired.

For a peak detection algorithm in accordance with an embodiment of the invention, an array of data points from a pulse oximeter probe, Data[ ], is acquired. Data[1000] contains 1000 samples of data acquired (as fast as possible). From the data contained in the array, peak detection can be carried out. During initialization the following variables' settings are made: Temp=Data[0] and flag is set to zero where Data[0]=Data[i=0]. Then, successive data points are analyzed for peaks. While consecutively iterating through the data, two cases exist. The first case (uphill movement A-B and downhill movement B-C) is illustrated in FIG. 5A and the second case (downhill movements B-C and C-D) is illustrated in FIG. 5B.

A downhill portion from the peak occurs where the data values are decreasing (i.e. Data[i]>Data[i+1]). A flag variable is used to differentiate between downhill movements B-C and C-D in order to define which of the downhill movements signifies a peak. The two downhill movements can each be 40 mV downhill (e.g., at a threshold indicating downward movement as opposed to noise); however, to determine whether an uphill movement (e.g., of 10 mV) preceded the downhill movement, a flag is used. In particular, the value of flag is set to 0 (flag=0) when the value of Temp increases, e.g., Temp goes from A to B. A value of flag=0 means the last step was an uphill movement of at least 10 mV. A value of flag=1 means the last step was a downhill movement.

In the first case, referring to FIG. 5A, A=Data[0]=Temp, and as iterations are performed over Data[ ], the value of Temp increases from A to B and the value of flag is set to 0. Going from B to C, the value of Temp decreases by 40 mV or more and the value of flag is 0; therefore, it can be determined that a peak occurred. The peak is counted (i.e., increment peak count; peak++) and the value of flag is set to 1 (flag=1).

In the second case, referring to FIG. 5B, Temp goes from C to D and the value of Temp decreased by 40 mV or more. However, the flag does not equal 0 at this time (due to the value of flag being set to 1 from the B to C movement) and hence this is not counted as a peak.

While going uphill from A to B, the values of Temp and flag are updated. If the value of Temp is less than Data[i]−10, Temp is updated (Temp=Data[i]) and the flag is set to 0 (flag=0).

In simple words, while going uphill (A to B), update the value of Temp=Data[i] and set the value of flag=0. While going downhill if the flag is equal to 0 and Temp decreases by 40 mV, count that as a peak and set the value of flag as 1.

While going uphill, the values of Temp and flag are updated only if the value of Temp increases by 10 mV, which causes the system to ignore the small noise peaks in the data (e.g., C' of FIG. 4).

The baseline shift in the signal is an induced perturbation. For example, a "raise your hand instruction," will drain blood from the fingers and lead to a baseline shift in what is called the DC component of the PPG. This baseline shift can be measured and can thus be interpreted as yet another means for detecting that the patient responded to a query. The different rates of rise and descent of artifacts with respect to the physiologic pulse sensed by the pulse oximeter can also be used to differentiate them from cardiac pulses and also from each other (e.g., NIBB cuff tap verses NIBP cuff squeeze). Accordingly, given a set of real time discrete data points (e.g, 1000 data points), the number of peaks can be analyzed and a determination made as to whether a patient provided a response. Pseudocode for the algorithm used for the prototype is shown as follows:

INPUT: Real Time Discrete Data Points
ALGORITHM: Collect 1000 data points in an array Data[1000] from the ACCESS I/O board.
Data[0]=A=Temp
Temp goes to B as Data[i] moves from A to B, i.e. while going uphill

```
If ( Data[i] >= Temp + 10 )
    Update Temp and set flag = 0
```

While going downhill, values of Temp and flag will be updated only when Temp>=Data[i]+40, and this counts as a peak i.e.

```
If(Temp >= Data[i] + 40)
    Temp = Data[i]
    if (flag = 0) {peak++; flag = 1;}
```

After iterating over 1000 samples, if the number of peaks is greater than 5, then it can be inferred that a deliberate finger shake occurred.

To set the sensitivity, the uphill threshold (i.e. 10 mV) can be changed, the downhill threshold (i.e. 40 mV) can be changed and the peaks limit can be increased from 5 to 6 or 7. The process can then be repeated for the next 1000 data points. In addition, the time period for sampling can also be increased.

```
Temp = Data[0]
For all Data points in Data
If( Temp + 10 <= Data[i])
{
    Temp = Data[i]
    Flag = 0;
}
Else{
    If(Temp >= Data[i] + 40)
    {
        Temp = Data
            If(Flag == 0)
            {
                Flag = 1;
                Peak++;
            }
    }
}
```

It should be noted that the simple algorithm described herein was for a proof of concept working model and is not optimized, nor does the simple algorithm address whether the photoplethysmogram and heart rate of the patient change under sedation and what effects these changes may have on the motion detection algorithm. In addition, other peak detection and various signal morphology (e.g., rise/decay, shape of peaks) methods can be used to identify artifacts in the signal. Localized curve fitting and standardized moments (e.g., skew and kurtosis), as well as low-pass filtering (such as downsampling and filtering) may be used.

Figure 6A:
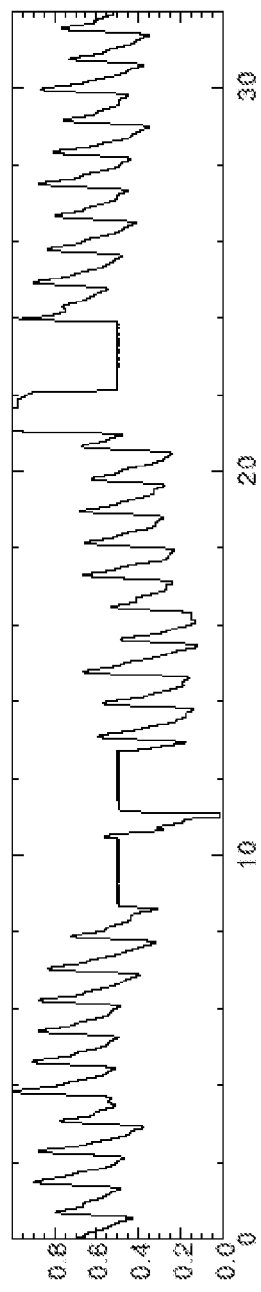
Figure 6B:
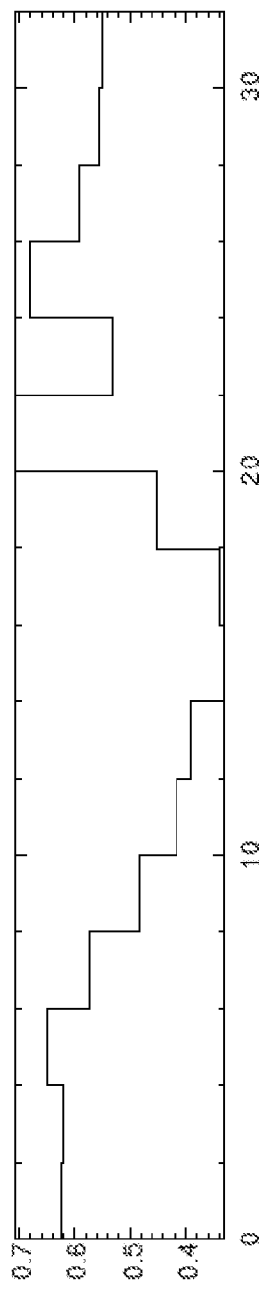
Figure 6C:
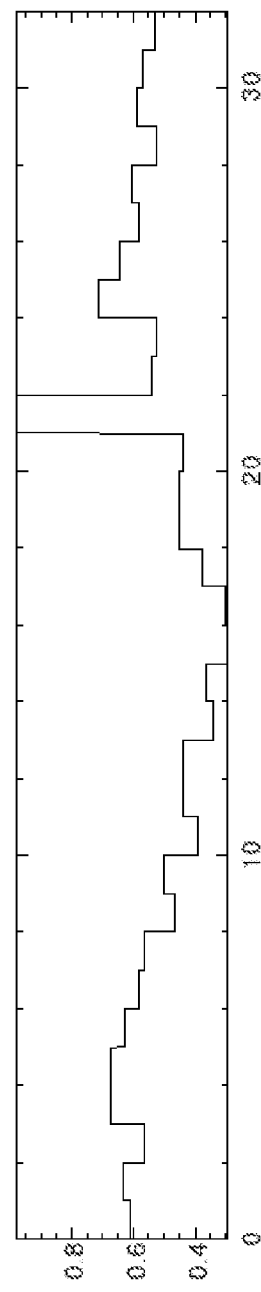

FIGS. 6A-6C and 7A-7C illustrate artifact identification for two subjects using a discrete wavelet transform approach instead of the simple peak detection described above. FIGS. 6A and 7A correspondingly show the raw signal from a pulse oximeter for a 10 second period of baseline, followed by a 10 second period of squeezing the pulse oximeter probe (a prolonged squeeze) and then a 10 second period without squeezing. FIGS. 6B and 7B show the Haar wavelet based approximation at a two second scale and FIGS. 6C and 7C show the Haar wavelet based approximation at a one second scale. The Haar wavelet based approximations were obtained by zeroing all detail at scales shorter than the scale of interest (e.g., 2 second and 1 second scaling) and then inverse-transforming the scaled signal to obtain a time-domain signal. In a similar manner, short time fast Fourier transforms (FFTs) can be used for detection of shaking.

According to certain embodiments for conscious sedation and consciousness monitoring, an initial learning baseline is performed in which a patient is asked NOT to move his or her finger. This baseline period can be helpful to address situations where the patient has a dicrotic notch (2 peaks instead of one per heartbeat) or a fast baseline heart rate. During the initial learning baseline, the number of peaks are counted per second at baseline for a given patient. It is then possible to later infer a deliberate artifact if the number of peaks per second increases by a certain amount or percentage above the baseline level within a given time window.

Figure 8A:
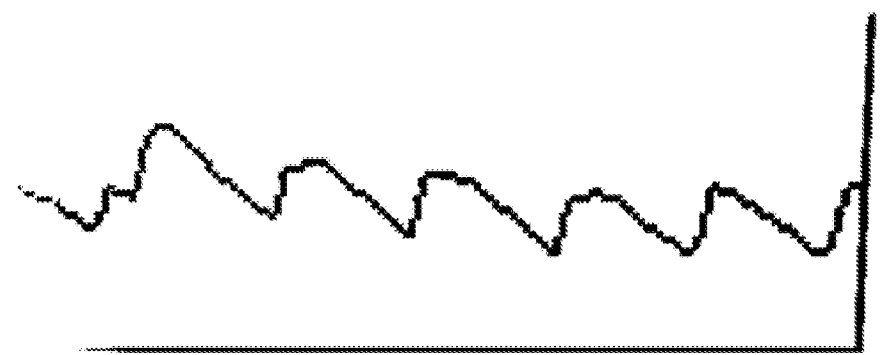
FIGS. 8A-8C show plethysmograms from a pulse oximeter in accordance with an embodiment of the invention.
Figure 8B:
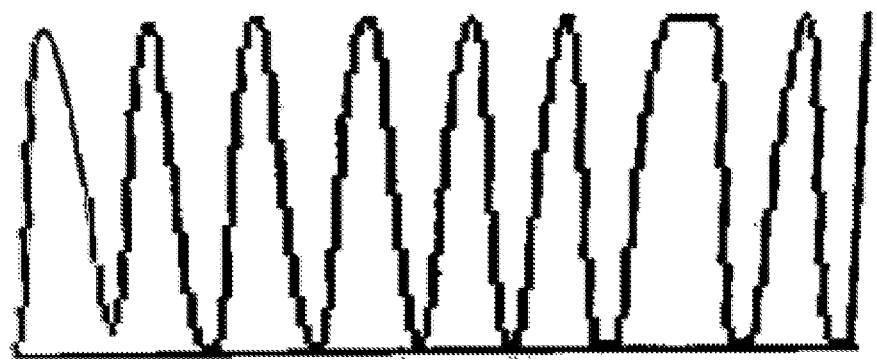
Figure 8C:
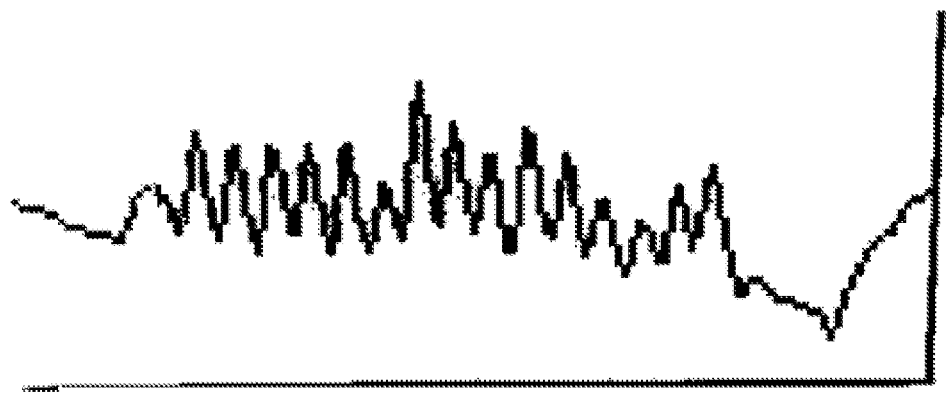

FIGS. 8A-8C show plethysmograms from a pulse oximeter in accordance with an embodiment of the invention. FIG. 8A shows a plethysmogram with no artifact, indicating no action by a patient. FIG. 8B shows a plethysmogram when a patient is squeezing the oximeter. The squeezing is cyclic (not constant); each hump corresponds to a squeeze and release of the finger. FIG. 8C shows a plethysmogram when a patient is shaking the finger with the oximeter probe. The finger shaking is also cyclic; each high frequency hump corresponds to a finger shake. The rate of rise and of descent of the artifacts can be differentiated from native signal and from window of time if in response to a prompt.

Figure 9A:
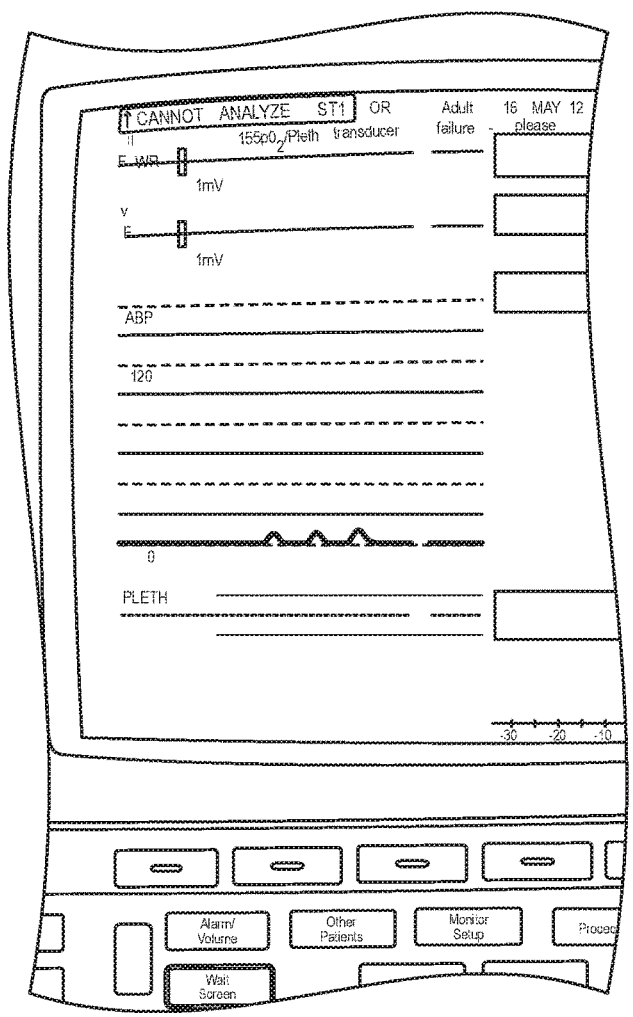
FIGS. 9A and 9B respectively show a photograph of a monitor with a pressure trace indicative of squeezing a deflated blood pressure cuff in accordance with an embodiment of the invention and a representation of the pressure trace signal.
Figure 9B:
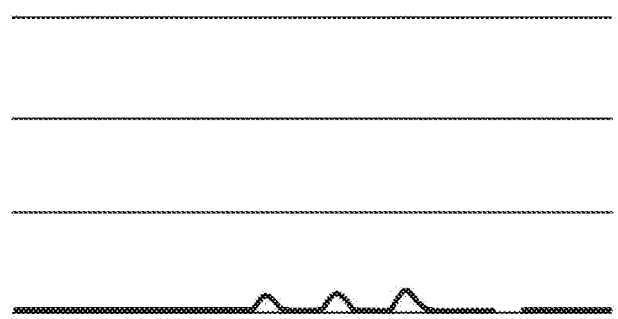
Figure 10A:
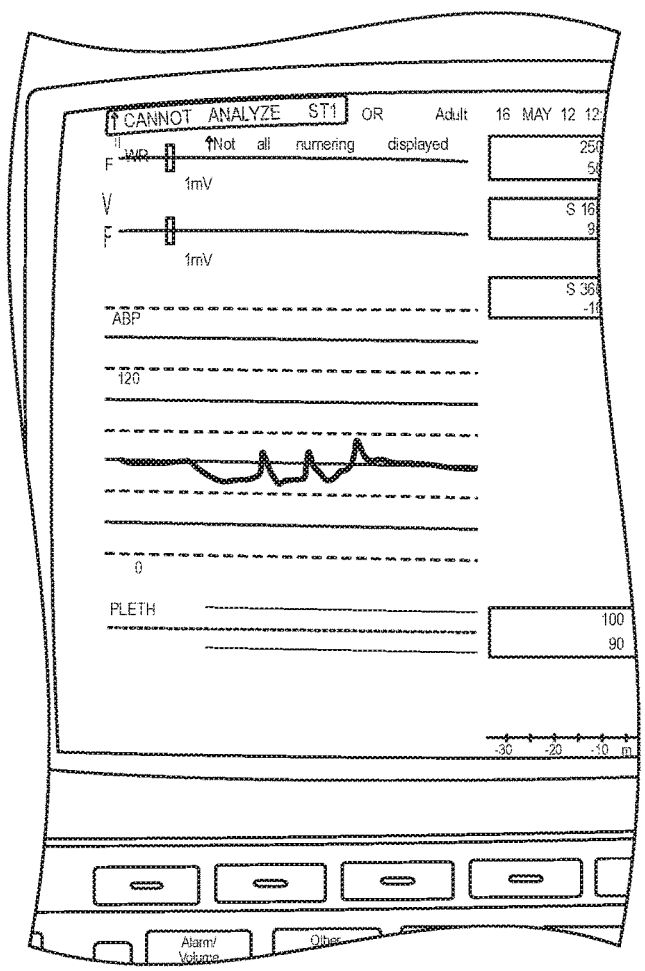
FIGS. 10A and 10B respectively show a photograph of a monitor with a pressure trace indicative of tapping a blood pressure cuff in accordance with an embodiment of the invention and a representation of the pressure trace signal.
Figure 10B:
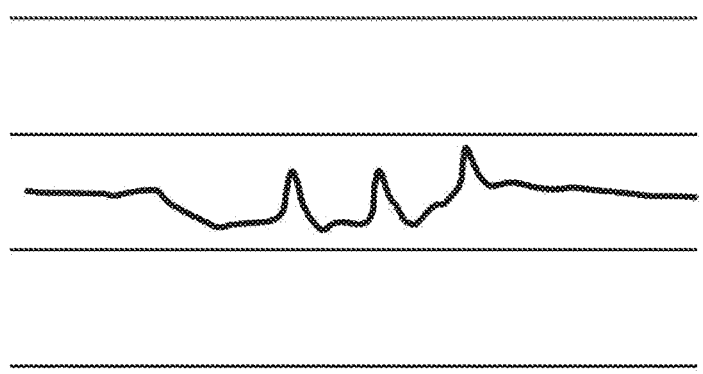

FIGS. 9A and 9B and 10A and 10B show examples of deliberate artifacts in existing monitoring equipment. In particular, pressure traces from a non-invasive blood pressure cuff are shown. FIGS. 9A and 9B illustrate the squeezing of the blood pressure cuff and FIGS. 10A and 10B illustrate tapping of the blood pressure cuff.

Once the initial learning baseline is performed, a quality control session is performed where the patient is prompted to wag his or her finger (or perform some other motion) in order to obtain an estimate of the frequency of peaks at motion for that patient. Instructions can be carried out using the device speaker. The quality control session can be used to verify that the many elements in the system are appropriate to allow reliable discrimination between response or no response to verbal commands and to establish a baseline time lag between the audio prompt and the detected response at full consciousness. Elements being verified include whether the speaker/communication is working properly, whether the volume is sufficiently loud for the patient to hear any prompts, whether the earbud was properly inserted, whether the patient suffers from hearing loss, selection of ear for the earbud (if using only one), comprehension of English or other language and vigor and frequency of the wagging, etc. If everything is working and no response is detected, it may be possible to teach the patient how to move their finger appropriately.

The prompt can be an audio prompt. For example, the pulse oximeter software can play an audio clip "Please, shake your finger" and then count the time between the audio prompt and the finger movement inferred from the detected motion artifact.

In one embodiment, after the audio prompt, the system can display the elapsed time in seconds and tenths of a second since the audio prompt. This display can be in graph form or using numbers. The system can indicate the units. For example, if the elapsed time is in seconds, the system can indicate that the units are in seconds. When the elapsed time is in tenths of a second, the display can indicate that the time is in tenths of a second by using any suitable nomenclature.

When motion is detected, the system can display an indication that motion was detected. For example, the system can output to the display "Responsive to verbal commands within y.z seconds." If there is no response detected after a predetermined period of time (e.g., 5 seconds or 15 seconds), the system can output to the display "Patient seems unresponsive to verbal commands; audio prompt is being repeated." At the elapsed predetermined period of time, the audio prompt can be repeated. The repeated audio prompt can be at a louder volume, at a different tone and/or include other stimulus. For example, the system can play an audio clip "Shake your finger NOW!" The second audio clip can be a different pre-recorded audio clip where the tone is more firm.

If there is no motion detected after first audio prompt and the second audio prompt, the system can output to the display "Patient unresponsive to verbal commands. Check patient immediately!" and sound an alarm. The alarm can be silenced or disabled once the patient is checked.

In certain embodiments, it can be beneficial to continuously monitor that a patient is conscious. In one such case, the first prompt (and second prompt, if needed) can be applied at a predetermined clinician-adjustable interval. For example, the patient can be prompted to respond every hour. The regular prompting can be useful for concussed patients.

A method of using libraries of queries, prompts and instructions and responses from the patient to enhance quality of care and patient safety is contemplated. Also contemplated is a method of marking prompted artifacts so that the artifacts can be distinguished from regular output data and, where needed, excluded from computed values such as averages and/or from medical records. For example, because blood pressure is averaged over time, it can be important for the deliberate artifacts to the blood pressure signal to not be included in the blood pressure values when monitoring the blood pressure. Accordingly, embodiments mark and remove the known deliberate artifacts from certain computed blood pressure values such as mean blood pressure before performing the calculations providing the mean blood pressure for the patient. This can help avoid misdiagnosis or other issues with the patient's medical records such as misinterpretation during medical malpractice litigation.

Further contemplated is a method of removing or reducing long time averaging time windows of certain monitoring devices during the response/query time frames so that computed values are quickly updated without delay. For example, certain monitoring devices perform averages of a physiological parameter over a certain window of time (for example, 15-30 seconds). This averaging causes a delay between an event and the output, which during normal operation is desirable. An example of an averaging window is during heart rate monitoring where heart rate irregularities in the beating of the heart are averaged over the time window to display a relatively stable heart rate that does not wildly fluctuate. A capnograph also utilizes an averaging time window. However, the prompted artifact data (such as an increased respiratory rate—RR—due to instructions to the patient to deliberately hyperventilate) during the expected response time from the patient may not appear because the window might not update the displayed numerical value for RR fast enough when the averaging window in used. Accordingly, embodiments provide a method in which the averaging window is temporarily disabled to obtain the instantaneous updates on certain values for the patient-in-the-loop response determination.

Prototype Example

Figure 11:
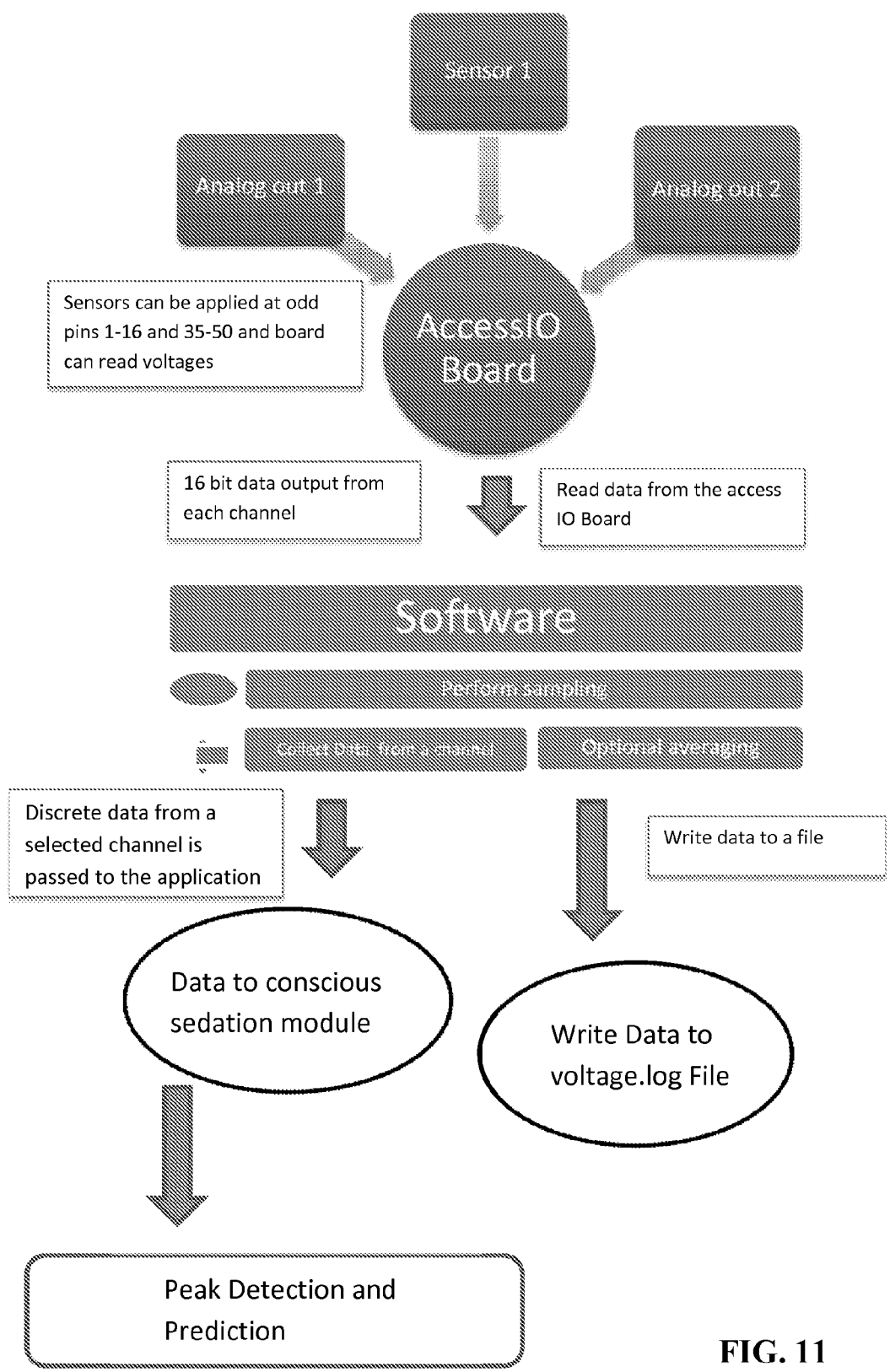
FIG. 11 shows a functional diagram of a system for consciousness monitoring in accordance with a prototype example of an embodiment of the invention.

FIG. 11 shows a functional diagram of the prototype example. As shown in FIG. 11, the ACCESS I/O board receives input from Analog out 1, Analog out 2, and the pulse oximeter sensor probe (Sensor 1). Real time data capture was obtained using the ACESS I/O board software functions ADC_GetScanV, which takes the data/voltage from across all the channels and dumps it into an array passed as a parameter, and ADC_GetChannelV, which takes the data/voltage across one specified channel and stores it into a double passed as a parameter.

For ADC_GetScanV( ), the first parameter is DeviceIndex which is usually zero for the experimental case and the second parameter (channeld) is the reference to an array into which the function dumps the data. Thus, where there are 16 channels:

double channeld[16];
ADC_GetScanV(DeviceIndex, channeld),

For ADC_GetChannelV( ), the first parameter is the DeviceIndex, the second parameter is the channel number from which the data is obtained, and the third parameter (chan) is the reference to variable into which the function stores the output value. Thus, when getting the voltage across channel 1 and storing the voltage to the chan variable, the function can be given as:

double chan;
ADC_GetChannelV(DeviceIndex,1,&chan).

The data can be written to a log file by using fprintf and fscanf functions to read and write from the file. Output will be stored in a "voltage.log" file.

The optional averaging can be carried out by averaging the data over a specified time period. In order to calculate the average before logging the data into a limited size log file, the following formula is used to calculate the average $A_n$ of the first n samples before logging (where $x_n$ is the nth sample).

$$A_n = \frac{n-1}{n}\left[A_{n-1} + \frac{x_n}{n-1}\right]$$

Once the data is collected from a channel, discrete data from a selected channel is passed to a conscious sedation module for peak detection and prediction of consciousness. For the prototype example, the conscious sedation module carries out the following peak detection algorithm. The peak detection algorithm was used to infer motion artifact in real time if there was more than x peaks (e.g, x=2) detected per 1 second time window. To show functionality, a KISS (keep it simple stupid), hard coded (>x peaks/s=motion) peak detection algorithm was used to detect the motion.

INPUT: Real Time Discrete Data Points
ALGORITHM: Collect 1000 data points in an array Data[1000] from the ACCESS I/O board. Under normal heartbeat, the number of peaks in this 1000 sample data set is expected to be 2-4.

Data[0]=A=Temp
Temp goes to B as Data[i] moves from A to B, i.e. while going uphill

```
If ( Data[i] >= Temp + 10 )
    Update Temp and set flag = 0
```

While going downhill, values of Temp and flag is updated only when Temp>=Data[i]+40, and this counts as a peak i.e.

```
If(Temp >= Data[i] + 40)
    Temp = Data[i]
    if (flag = 0) {peak++; flag = 1;}
```

After iterating over 1000 samples, if the number of peaks is greater than 5, this can be inferred as a finger shake.

According to the algorithm, the motion artifact detection involves searching for the large peaks (beyond those caused by the cardiac pulse) that are added by finger shaking (motion artifact) to the analog photoplethysmogram data acquired via the ACCESS I/O board and discarding the small peaks caused by noise. If the height of the peak is greater than 10 mV while rising up AND greater than 40 mV while going down, then the peak is counted as a peak otherwise the peak is considered as noise. However, these 10 mV and 40 mV thresholds are programmable and can be set and adjusted inside the program code. In a normal data collected over 1000 samples iteration, the data would contain 2-4 peaks; however during data acquisition, if the user is shaking his or her finger, the number of peaks in the data would be greater than 5. If the number of peaks detected is greater than 5, then it can be concluded that the user was shaking the finger. However the number of peaks also depends upon factors such as the values of the thresholds with default values of 10 and 40 mV, the baseline heart rate and the typical photoplethysmogram characteristics (for example, noise content and presence or absence of a dicrotic notch) of the patient.

Figure 12:
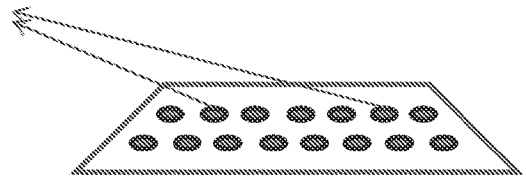
FIG. 12 provides a representation of a pulse oximeter monitor pin out.

FIG. 12 provides a representation of a pulse oximeter monitor pin out. The pins are symmetrical; therefore, swapping the two data output pins provides a negative voltage. Pin 14 is positive and pin 10 is Ground in the DB15 connector at the back of the pulse oximeter. The Nellcor™ pulse oximeter monitor used for the experiment has a maximum signal amplitude of 1000 mV and an average amplitude that ranges between 300-600 mV for normal heart beat people.

Figure 13A:
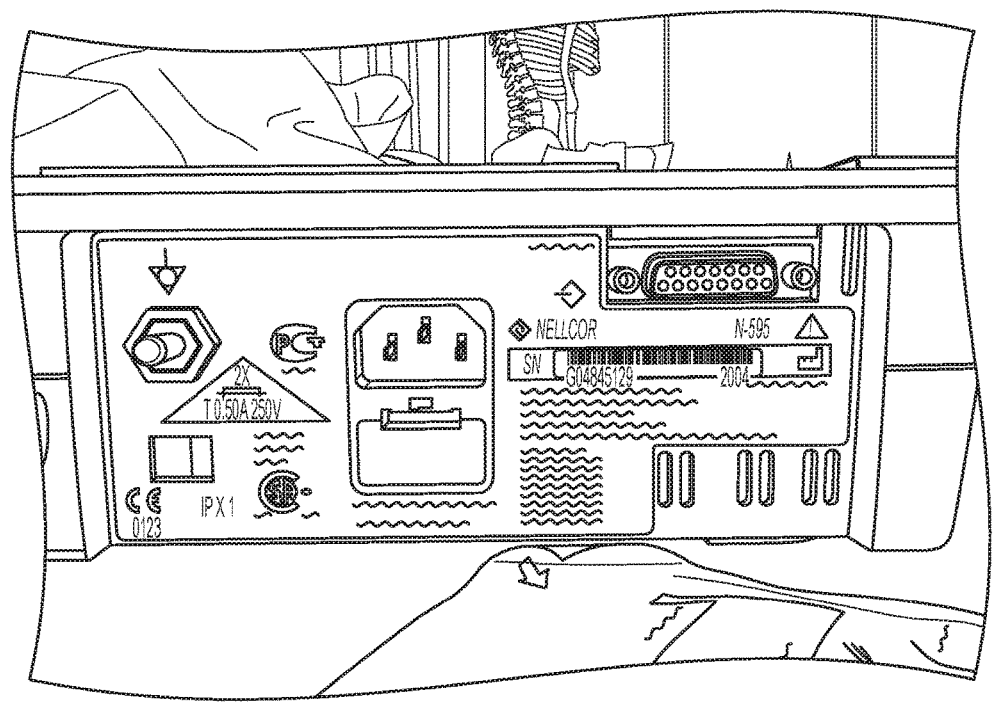
FIGS. 13A-13E are photographs of a prototype embodiment of the system for consciousness assessment of an embodiment of the invention.
Figure 13B:
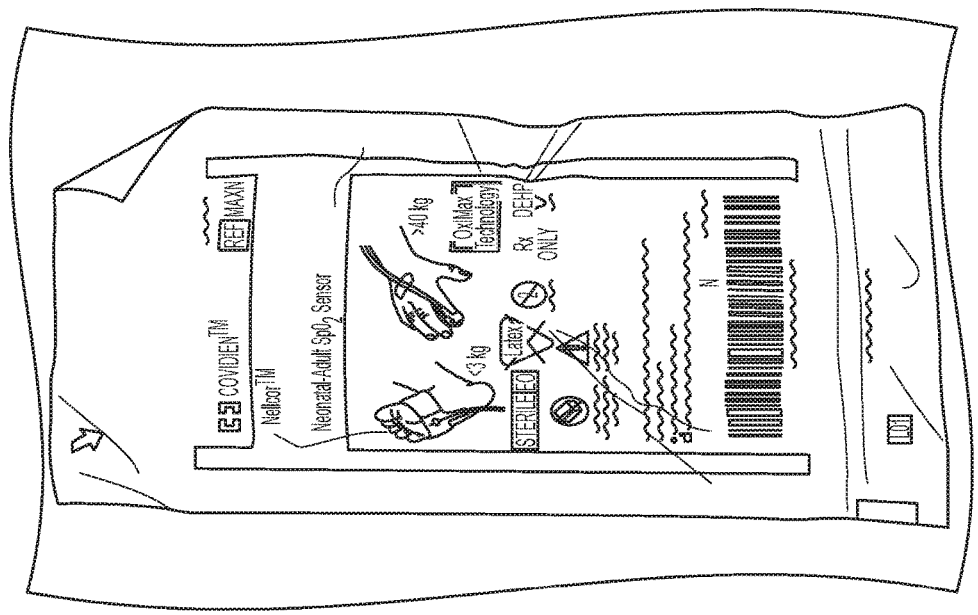
Figure 13C:
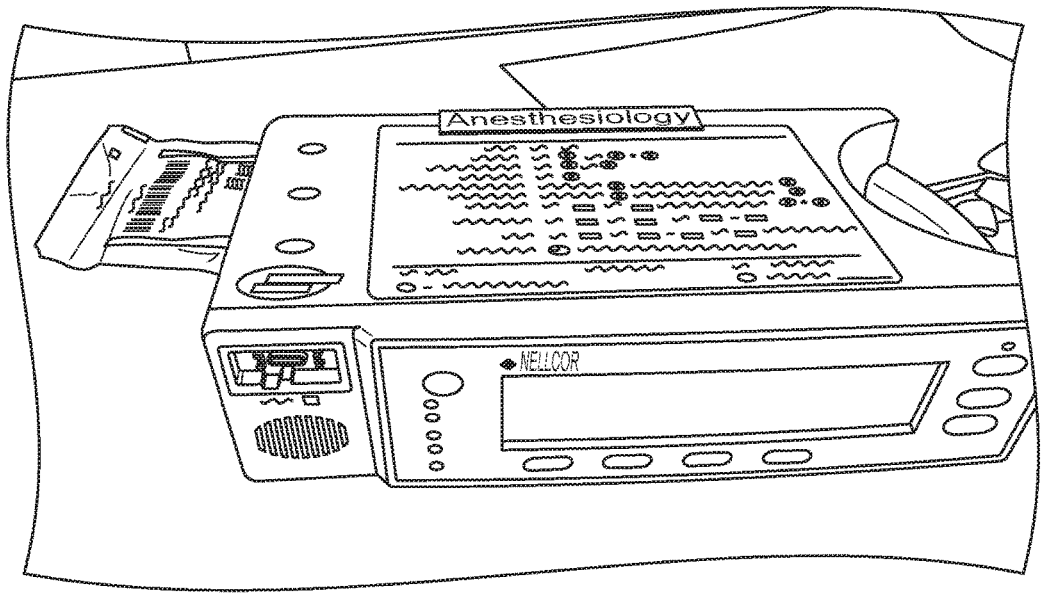
Figure 13D:
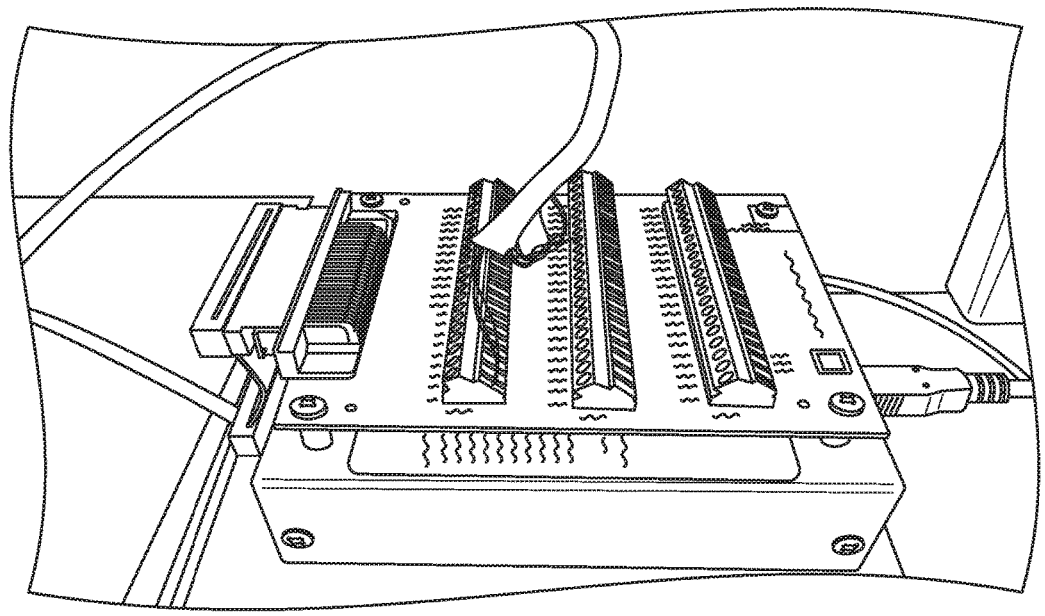
Figure 13E:
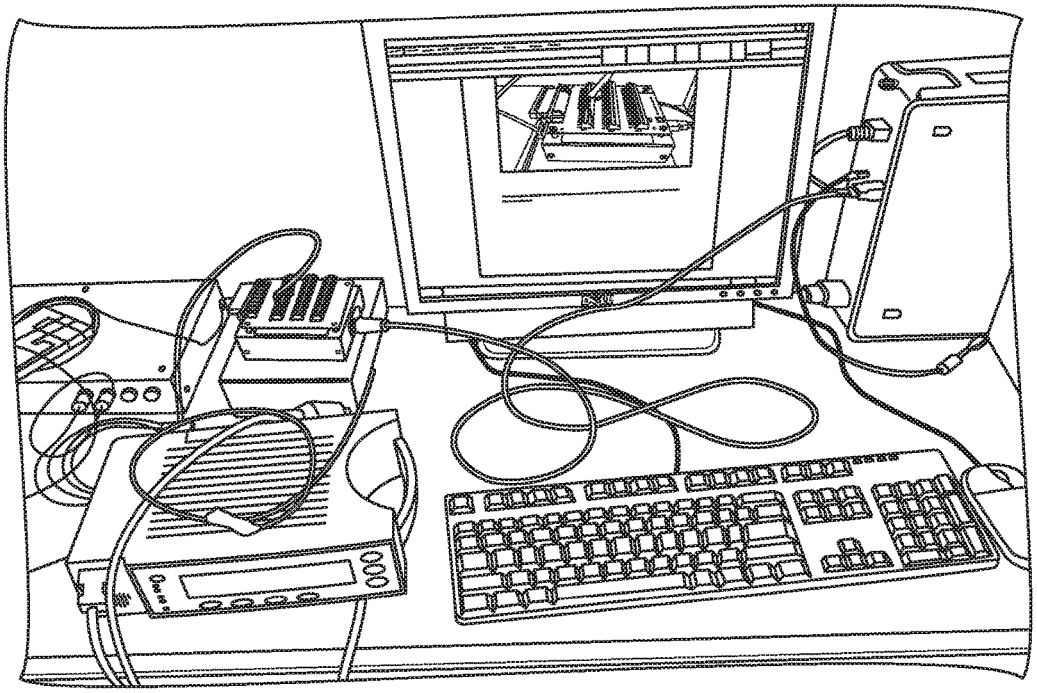

FIGS. 13A-13E show photographs of the experimental set-up. As shown in FIG. 13A, two pins (per the diagram shown in FIG. 12) in the DB 15 connector at the top right of the back panel provide the photoplethysmogram in analog form. The prototype example included a computer platform; an ACCESS (Acquisition Control Communication Engineering/Systems) I/O Board USB-AI16-16A from ACCES I/O Products, Inc.; the Nellcor™ pulse oximeter N-595 SN: G04845129; and Nellcor™ Adult SpO2 Sensor 1238033X. The Nellcor™ products are affiliated with a Covidien company.

For patient-in-the-loop participatory care, the patient can be determined to have complied with a request such as take a deep breath by detecting and interpreting the desired artifact in one or more monitors within a given time window. In instances of patient-in-the-loop participatory care where the action of the patient when complying with a request may not produce a reliably detectable artifact with the monitors that are typically used (such as shifting one's weight to prevent pressure sores), the patient can be asked to confirm after a given elapsed time that is sufficient to perform the action, whether the action was indeed performed and this can then be recorded (and marked/distinguished as a patient-entered data verses a clinician-entered data).

Figure 14:
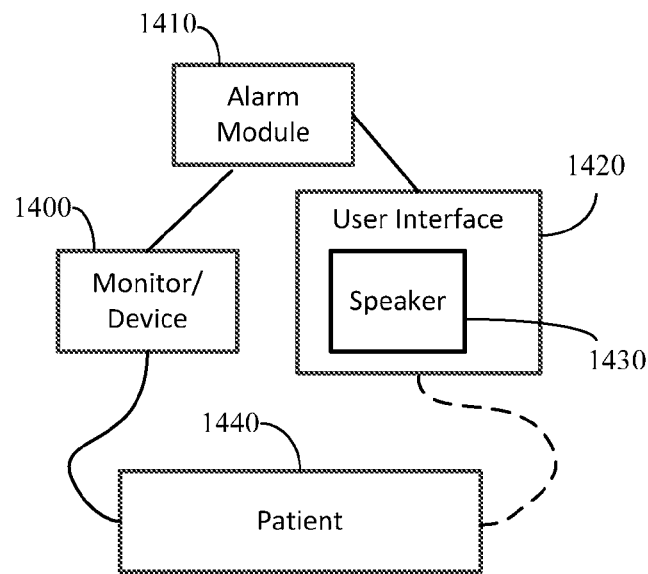
FIG. 14 shows a diagram of a patient-in-the-loop system enabling self-correction for reducing certain alarms in accordance with an embodiment of the invention.

In some embodiments, monitoring devices can utilize a patient-in-the-loop approach to enable self-correction for alarms. FIG. 14 shows a diagram of a patient-in-the-loop system enabling self-correction for reducing certain alarms in accordance with an embodiment of the invention. Referring to FIG. 14, a self-correction may be accomplished through a monitoring device (or other device) 1400; alarm module 1410; and user interface 1420, which may involve a speaker 1430 (and/or a display).

The monitoring device (or other device) 1400 may sense an impending condition and according to the control of an alarm module 1410, instruct (via the user interface 1420) the patient, as first resort, to make a self-corrective maneuver. Certain alarm conditions can be corrected and/or addressed before sending an alarm to bring a clinician to the patient by outputting at the monitoring device (where the monitoring device includes the alarm module and user interface) or some other healthcare environment device (providing a user interface/speaker) to which the monitoring device can communicate with, an alarm or request to a patient to respond to instructions such as take a deep breath, shift your weight, keep your finger still, straighten your arm, move your leg(s), and the like.

For example, an oximeter or other monitor may, in response to a determination that oxygen saturation is declining, alert and/or prompt the patient to take several deep breaths. If the patient follows the instruction and/or the oxygen saturation increases and/or returns to an appropriate level, the alarm to a clinician or other health care provider may be avoided. However, if the corrective maneuver does not provide the desired result (or no corrective maneuver is performed by the patient) within a period of time (or the levels pass a certain threshold), the alarm will be activated. By providing an opportunity for patient corrective measures prior to sounding an alarm, alarm fatigue may be substantially reduced.

Figure 15:
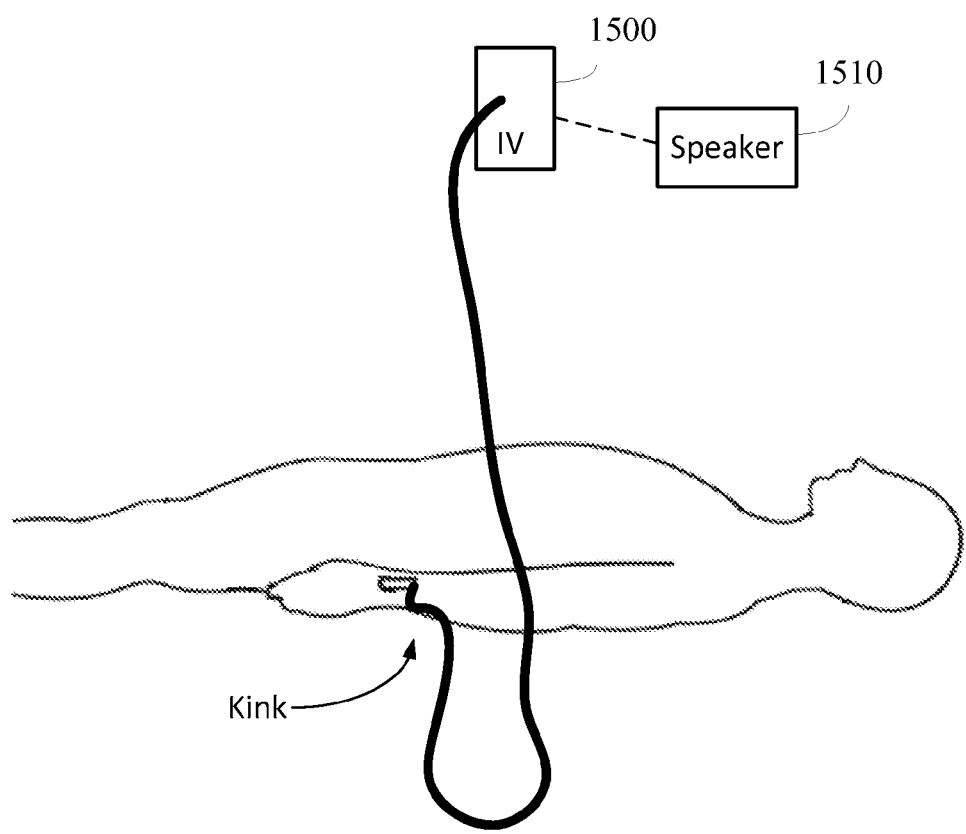
FIG. 15 illustrates an example implementation of a system enabling self-correction for reducing certain alarms.

As another example, such as illustrated in FIG. 15, a kink may exist in an IV line. One illustrative implementation for when a kink occurs, involves the kink being detected by the IV pump's software, which may currently indicate detection as a visual yellow (no audio) caution alarm (generally stays on for 15 seconds). If within those 15 seconds, the occlusion is not cleared, the visual alarm may turn from yellow to red and an audible alarm will also be sound. Occlusion of IV tubing may be the single most common source of IV pump alarms. Therefore, according to an embodiment, there is an opportunity to correct the occlusion before an audible alarm is sound or immediately after the audible alarm is sound (but in some cases before a secondary alert is provided). In response to an infusion pump (e.g., IV pump 1500) measuring a rise in the outflow pressure of the IV (which may indicate a downstream occlusion alarm is forthcoming), the IV pump (directly or through a device or system that the IV pump communicates with) may alert or instruct the patient to straighten the body part with the IV. The alert may be output via a speaker 1510 or other user interface in communication with the IV pump. The IV pump can be considered a controlling device as it is trying to control a patient condition such as pain level by administering pain medication. Both monitoring and controlling devices fall under patient care devices as well as any other devices used in patient care.

Certain techniques set forth herein may be described in the general context of computer-executable instructions, such as program modules, executed by one or more computers or other devices. Certain embodiments of the invention contemplate the use of a computer system or virtual machine within which a set of instructions, when executed, can cause the system to perform any one or more of the methodologies discussed above. Generally, program modules include routines, programs, objects, components, and data structures that perform particular tasks or implement particular abstract data types.

It should be appreciated by those skilled in the art that computer-readable media include removable and non-removable structures/devices that can be used for storage of information, such as computer-readable instructions, data structures, program modules, and other data used by a computing system/environment. A computer-readable medium can be a memory device including, but not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); or other media now known or later developed that is capable of storing computer-readable information/data. Computer-readable media should not be construed or interpreted to consist of propagating signals.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

We claim:

1. A method of patient participatory care and monitoring, comprising:
    querying, instructing, or prompting a patient based on a query library to provide a response by prompting performance of an act by the patient that results in deliberate introduction of an artifact into a signal or inaction by the patient that results in no-artifact or cessation of the patient-introduced artifact;
    receiving the signal from a device monitoring, controlling, or sensing a condition of the patient; and
    analyzing the signal from the device based on the presence, absence of a patient-introduced artifact, or cessation of the patient-introduced artifact and on a response library to determine the patient's response.

2. The method according to claim 1, wherein the querying, instructing or prompting of the patient is performed without active involvement from or in the absence of a healthcare worker.

3. The method according to claim 1, further comprising: displaying the response of the patient on a monitor.

4. The method according to claim 1, wherein querying, instructing or prompting a patient to provide the response comprises:
outputting, via a speaker, at least one audio prompt, instruction or query.

5. The method according to claim 4, wherein outputting the at least one audio prompt instruction or query is performed according to a predetermined interval to periodically request a response from the patient, the response from the patient being determined by analyzing the signal from the device.

6. The method according to claim 1, wherein analyzing the signal from the device comprises analyzing artifacts in the signal indicating the condition or response of the patient being monitored, controlled or sensed.

7. The method according to claim 6, wherein analyzing the signal from the device is performed within a specified time window after the querying, instructing or prompting.

8. The method according to claim 6, wherein the device is a pulse oximeter, wherein the signal is received from a pulse oximeter probe, wherein analyzing artifacts in the signal comprises performing a peak analysis, filtering, or transform of the signal from the pulse oximeter probe to determine whether the patient had shaken or squeezed a finger on which the pulse oximeter probe is placed.

9. The method according to claim 6, wherein the device is a non-invasive blood pressure monitor, wherein the signal is received from a blood pressure cuff of the non-invasive blood pressure monitor, wherein analyzing artifacts in the signal comprises performing a peak analysis, filtering, or transform of the signal from the blood pressure cuff to determine whether the patient had squeezed or tapped the blood pressure cuff.

10. The method according to claim 1, further comprising:
in response to detecting an initial pre-alarm or an impending alarm condition from the signal from the device, querying, instructing, or prompting the patient to perform a remedial action without active involvement from or in the absence of a healthcare worker.

11. The method according to claim 1, wherein the device is an infusion pump or a pulse oximeter.

12. The method according to claim 1, further comprising:
providing data related to a patient's response or actions to an electronic medical records system.

13. The method according to claim 1, further comprising:
performing a learning baseline to establish baseline measures indicative of no-artifact and deliberate artifact carried out by the patient; and
performing a quality control session verifying that the device is appropriate to allow reliable discrimination between response and no response.

14. The method according to claim 13, wherein analyzing the signal from the device comprises analyzing artifacts in the signal indicating the condition or response of the patient being monitored, controlled or sensed, and
wherein the baseline measures are stored in a memory and accessed during the analyzing of the artifacts in the output signal to interpret and determine the patient's response.

15. The method according to claim 14, wherein the device is an existing device, and
wherein the method is implemented on a retrofit kit on the existing device.

16. The method according to claim 15, wherein the retrofit kit does not interfere with operation of the existing device and reads a status of the existing device via electronic communication or via a photodetector monitoring the status of the existing device.

17. A patient in-the-loop monitoring system comprising:
a memory device; and
a processor for reading data received from a pulse oximeter probe via an I/O port, storing the data at a first location in the memory device, and analyzing the data stored at the first location based on a response library to determine whether the patient deliberately manipulated artifacts in the data from the pulse oximeter probe,
wherein the data is the result of querying, instructing, or prompting the patient based on a query library to provide a response by prompting performance of an act by the patient that results in deliberate introduction of an artifact into a signal or inaction by the patient that results in no-artifact or cessation of the patient-introduced artifact.

18. The system according to claim 17, wherein the processor further outputs queries and prompts stored at a second location in the memory device to the patient via a speaker.

19. The system according to claim 17, further comprising a monitor, wherein the processor outputs an image or data for display on the monitor.

20. The system according to claim 17, wherein the processor further:
performs a learning baseline to establish baseline measures indicative of no-artifact and deliberate artifact carried out by a patient; and
performs a quality control session verifying that a device is appropriate to allow reliable discrimination between response and no response.

21. The system according to claim 20, wherein the system is implemented as a retrofit kit on a pulse oximeter having the I/O port providing data from the pulse oximeter probe.

22. The system according to claim 21, wherein the retrofit kit does not interfere with operation of the pulse oximeter and reads a status of the pulse oximeter via electronic communication or via a photodetector.

23. A non-transitory computer-readable medium having instructions stored thereon that, when executed, cause a processor to perform a method of patient participatory monitoring and care comprising:
outputting, via a speaker, at least one query or audio prompt to query, instruct, or prompt a patient based on a query library to provide a response by prompting performance of an act by the patient that results in deliberate introduction of an artifact into a signal or inaction by the patient that results in no-artifact or cessation of the patient-introduced artifact;
receiving data from the patient during a time period for providing the response;
performing a learning baseline to establish baseline measures indicative of no-artifact and deliberate artifact carried out by the patient;
performing a quality control session verifying that a device is appropriate to allow reliable discrimination between response and no response; and
analyzing artifacts in the data based on a response library to determine the patient's response.

24. The non-transitory computer-readable medium according to claim 23, further comprising instructions for displaying the patient's response on a monitor.

25. The non-transitory computer-readable medium according to claim 23, wherein outputting the at least one query or audio prompt is performed according to a predetermined interval to periodically request a response from the patient, the response from the patient being determined by analyzing the artifacts in the data.

26. The non-transitory computer-readable medium according to claim 23, wherein analyzing artifacts in the data comprises performing a peak analysis, filtering or transform of the data to determine whether the patient had deliberately manipulated the probe.

27. The non-transitory computer-readable medium according to claim 23, wherein the method performed by the processor further comprises:

performing a learning baseline to establish baseline measures indicative of no-artifact and deliberate artifact carried out by the patient; and performing a quality control session verifying that a device is appropriate to allow reliable discrimination between response and no response.

28. The non-transitory computer-readable medium according to claim 27, wherein the device is an existing device, and wherein the non-transitory computer-readable medium is implemented on a retrofit kit on the existing device.

29. The non-transitory computer-readable medium according to claim 28, wherein the retrofit kit does not interfere with operation of the existing device and reads a status of the existing device via electronic communication monitoring the status of the existing device.

* * * * *